US010639266B2

(12) United States Patent
Yoneto

(10) Patent No.: US 10,639,266 B2
(45) Date of Patent: May 5, 2020

(54) WATER-SOLUBLE HYALURONIC ACID GEL AND METHOD FOR PRODUCING SAME

(71) Applicant: RITAPHARMA, CO., LTD., Shimogyo-ku, Kyoto-shi, Kyoto (JP)

(72) Inventor: Kunio Yoneto, Kyoto (JP)

(73) Assignee: RITAPHARMA, CO., LTD, Kyoto-shi (JP)

( * ) Notice: Subject to any disclaimer, the term of this patent is extended or adjusted under 35 U.S.C. 154(b) by 0 days.

(21) Appl. No.: 14/892,282

(22) PCT Filed: Jun. 27, 2014

(86) PCT No.: PCT/JP2014/067199
§ 371 (c)(1),
(2) Date: Nov. 19, 2015

(87) PCT Pub. No.: WO2015/002091
PCT Pub. Date: Jan. 8, 2015

(65) Prior Publication Data
US 2016/0081906 A1  Mar. 24, 2016

(30) Foreign Application Priority Data

Jul. 3, 2013 (JP) ................................ 2013-139624
Dec. 9, 2013 (JP) ................................ 2013-253769

(51) Int. Cl.
| A61K 8/04 | (2006.01) |
| A61K 8/24 | (2006.01) |
| A61K 8/34 | (2006.01) |
| A61K 8/73 | (2006.01) |
| A61K 9/06 | (2006.01) |
| C08K 3/24 | (2006.01) |
| C08K 5/09 | (2006.01) |
| C08L 5/08 | (2006.01) |
| A61K 47/10 | (2017.01) |
| A61K 47/36 | (2006.01) |
| A61Q 19/00 | (2006.01) |
| C08B 37/08 | (2006.01) |
| C08J 3/075 | (2006.01) |
| A61K 31/728 | (2006.01) |

(52) U.S. Cl.
CPC .............. *A61K 8/735* (2013.01); *A61K 8/042* (2013.01); *A61K 8/24* (2013.01); *A61K 8/34* (2013.01); *A61K 8/345* (2013.01); *A61K 9/06* (2013.01); *A61K 31/728* (2013.01); *A61K 47/10* (2013.01); *A61K 47/36* (2013.01); *A61Q 19/00* (2013.01); *A61Q 19/007* (2013.01); *C08B 37/0072* (2013.01); *C08J 3/075* (2013.01); *C08K 3/24* (2013.01); *C08K 5/09* (2013.01); *C08L 5/08* (2013.01); *C08J 2305/08* (2013.01)

(58) Field of Classification Search
CPC .... C08L 5/08; C08K 3/24; C08K 5/09; A61K 31/728; A61K 47/10; A61K 47/36; A61K 8/042; A61K 8/24; A61K 8/34; A61K 8/345; A61K 8/735; A61K 9/06; A61Q 19/00; A61Q 19/007; C08B 37/0072; C08J 2305/08; C08J 3/075
See application file for complete search history.

(56) References Cited

U.S. PATENT DOCUMENTS

| 5,827,937 A | 10/1998 | Ågerup |
| 6,025,444 A | 2/2000 | Waki et al. |
| 6,107,410 A | 8/2000 | Waki et al. |
| 2002/0098244 A1 | 7/2002 | Miyata et al. |
| 2006/0105022 A1 | 5/2006 | Yokokawa et al. |
| 2006/0110352 A1* | 5/2006 | Milbradt ............. A61K 8/8158 424/70.15 |
| 2008/0169215 A1 | 7/2008 | Tanaka et al. |
| 2010/0210587 A1 | 8/2010 | Matsumoto |
| 2011/0034684 A1 | 2/2011 | Yokokawa et al. |
| 2011/0110874 A1 | 5/2011 | Tanaka et al. |

FOREIGN PATENT DOCUMENTS

| CN | 101418049 A | 4/2009 | |
| CN | 101821294 A | 9/2010 | |
| EP | 1 281 722 A1 | 2/2003 | |
| JP | 5-58881 A | 3/1993 | |
| JP | 6-65048 A | 3/1994 | |
| JP | 8-143604 A | 6/1996 | |
| JP | 9-110680 A | 4/1997 | |
| JP | 11-509256 A | 8/1999 | |
| JP | 2002-212047 A | 7/2002 | |
| JP | 2009-102228 A | 5/2009 | |
| JP | 2009102228 A * | 5/2009 | ............... A61K 8/25 |
| JP | 2010-515720 A | 5/2010 | |
| JP | 2011-136936 A | 7/2011 | |
| JP | 2011136936 A * | 7/2011 | ............. A61K 8/368 |
| JP | 2013-107862 A | 6/2013 | |
| JP | 2014-24828 A | 2/2014 | |
| WO | 99/10385 A1 | 3/1999 | |
| WO | 01/57093 A1 | 8/2001 | |
| WO | 2006/015950 A1 | 2/2006 | |

OTHER PUBLICATIONS

English machine translation of Yamada et al. (JP2009102228A; published May 14, 2009) made Jan. 4, 2017.*
International Search Report dated Sep. 22, 2014, issued in counterpart International Application No. PCT/JP2014/067199 (3 pages).
Office Action dated Aug. 24, 2017, issued in Taiwanese Application No. 103122835 (7 pages).
Office Action dated Feb. 5, 2019, issued in counterpart Japanese Application No. 2015-525188, with partial English translation. (6 pages).

* cited by examiner

*Primary Examiner* — Michael B. Pallay
(74) *Attorney, Agent, or Firm* — Westerman, Hattori, Daniels & Adrian, LLP

(57) ABSTRACT

To provide a water-soluble hyaluronic acid gel which does not contain a large amount of an organic solvent, wherein hyaluronic acid is not chemically modified.
A water-soluble hyaluronic acid gel which contains hyaluronic acid, a polyhydric alcohol, an acid, and 0-10% by mass of a water-soluble organic solvent.

18 Claims, No Drawings

WATER-SOLUBLE HYALURONIC ACID GEL AND METHOD FOR PRODUCING SAME

TECHNICAL FIELD

The present invention relates to a water-soluble hyaluronic acid gel and a method for producing the water-soluble hyaluronic acid gel.

BACKGROUND ART

In recent years, hyaluronic acid, which has excellent biocompatibility and also has many beneficial effects including a moisturizing effect, has been focused in the cosmetology field, the medical field and the like. Hyaluronic acid is a linear high-molecular-weight polysaccharide in which β-D-N-acetylglucosamine and β-D-glucuronic acid are bound alternately, and is known to distribute in connective tissues in mammals and also distribute in chicken's combs, streptococcal capsules and the like. Commercially available products of hyaluronic acid are generally prepared by the isolation/extraction from chicken's combs, umbilical cords or the like, a fermentation method using a microorganism such as a microorganism belonging to the genus *Streptococcus*, and the like.

Gel compositions each containing a high-molecular-weight material have been used conventionally in the cosmetology field, the medical field and the like. In particular, gel compositions which are intended to be used in the cosmetology field, the medical field and the like are applied to human bodies and therefore are required to have excellent biocompatibility. For these reasons, it has been considered to use hyaluronic acid, which is a naturally occurring material and has excellent biocompatibility, as a high-molecular-weight material to be contained in the gel compositions.

In Patent Document 1, for example, a method for preparing a gel composition using crosslinked hyaluronic acid is disclosed. In Patent Document 2, a gel of a photocrosslinkable hyaluronic acid derivative is disclosed, which is characterized in that 0.0005 to 0.05 piece on average of a photodimerizable crosslinking group is introduced per two hyaluronic acid-constituting sugar units. In Patent Document 3, a method for producing a crosslinked hyaluronic acid gel is disclosed, which is characterized by agitating/mixing a mixture comprising 10 W/V % or more of hyaluronic acid, a cross-linking agent and water under acidic or alkaline conditions.

However, as disclosed in Patent Documents 1 to 3, chemically modified hyaluronic acid is used in most of the conventional gel compositions prepared using hyaluronic acid. Therefore, the conventional gel compositions have a problem that the characteristic properties inherent in hyaluronic acid as a naturally occurring material are lost.

Furthermore, in Patent Document 4 for example, a method for producing a hyaluronic acid gel is disclosed, which is characterized in that hyaluronic acid is allowed to co-exist together with both water in such an amount that the concentration of hyaluronic acid can become 5% by mass or more and an acid component in an equimolar amount to a carboxyl group in hyaluronic acid or more and the co-existing state is retained, thereby producing the hyaluronic acid gel. However, the hyaluronic acid gel produced in Patent Document 4 is poorly soluble in water, and therefore hyaluronic acid can be hardly eluted into water. Therefore, a poorly water-soluble hyaluronic acid gel as disclosed in Patent Document 4 is deteriorated in the effect induced by hyaluronic acid contained therein, i.e., impartment of moistness and springiness to skin, when applied onto skin, and therefore is improper for use in the cosmetology field and the like. Furthermore, the hyaluronic acid gel disclosed in Patent Document 4 is produced by allowing hyaluronic acid, an acid and water to stand for at least several days under low-temperature conditions, and therefore has a problem that a long period of time is required for the production of the hyaluronic acid gel.

In Patent Document 5 for example, a matter that a hyaluronic acid gel is produced by bringing a hyaluronic acid solution into contact with a water-soluble organic solvent, such as methanol, ethanol, isopropanol and acetone, under conditions having a pH value of 2.0 to 3.8 is disclosed. In the method disclosed in Patent Document 5, however, the water-soluble organic solvent is contained in a large amount in the hyaluronic acid gel, and therefore the hyaluronic acid gel has a problem that the hyaluronic acid gel is hardly used in the cosmetology field, the medical field and the like. In the cosmetology field, the medical field and the like, a sheet made from a gel composition is advantageous because the sheet can be applied onto skin easily. However, the hyaluronic acid gel disclosed in Patent Document 5 has an additional problem that the hyaluronic acid gel cannot be made into a sheet-like form easily by a simple method such as a cast method.

PRIOR ART DOCUMENTS

Patent Documents

Patent Document 1: Japanese Unexamined Patent Application Publication (Translation of PCT Application) No. 11-509256

Patent Document 2: Japanese Patent Application Laid-open No. 8-143604

Patent Document 3: International Publication No. 2006-051950 pamphlet

Patent Document 4: International Publication No. 01/57093 pamphlet

Patent Document 5: Japanese Patent Application Laid-open No. 5-5881

SUMMARY OF THE INVENTION

Problems to be Solved by the Invention

The main purpose of the present invention is to provide a water-soluble hyaluronic acid gel in which hyaluronic acid is not chemically modified and a large amount of an organic solvent is not contained. Another purpose of the present invention is to provide: a method for producing the water-soluble hyaluronic acid gel; and a cosmetic, a pharmaceutical composition for external applications or a composition for medical tools each comprising the water-soluble hyaluronic acid gel.

Means for Solving the Problems

The present inventors have made intensive and extensive studies for the purpose of solving the problems. As a result, it is found that a water-soluble hyaluronic acid gel containing hyaluronic acid, a polyhydric alcohol, an acid and 0 to 10% by mass of a water-soluble organic solvent can have a form of a gel even when hyaluronic acid is not chemically modified and the organic solvent is not contained in a large amount therein. This finding is amazing, because the conventional known hyaluronic acid gels are those which are produced using chemically modified hyaluronic acid, those which are poorly soluble in water, those which are required to use large amounts of organic solvents, and so on. Furthermore, it is also found that the water-soluble hyaluronic acid gel can be produced conveniently by a method involving a step of mixing hyaluronic acid, a polyhydric alcohol, an acid, 0 to 10% by mass of a water-soluble organic solvent and water together. The present invention has been accomplished by making further studies on the basis of the above-mentioned findings.

That is, the present invention provides the below-mentioned embodiments of the inventions.

1. A water-soluble hyaluronic acid gel comprising hyaluronic acid, a polyhydric alcohol, an acid and 0 to 10% by mass of a water-soluble organic solvent.

2. The water-soluble hyaluronic acid gel according to item 1, wherein an aqueous hyaluronic acid solution has a pH value falling within the range from 1.9 to 5.2, in which the aqueous hyaluronic acid solution is prepared by dissolving the components to be contained in the water-soluble hyaluronic acid gel, except the polyhydric alcohol and water, in water in such a manner that 200 parts by mass of water is contained relative to 1 part by mass of hyaluronic acid contained in the water-soluble hyaluronic acid gel.

3. The water-soluble hyaluronic acid gel according to item 1 or 2, wherein the content of hyaluronic acid is 0.04 to 50% by mass.

4. The water-soluble hyaluronic acid gel according to any one of items 1 to 3, wherein the polyhydric alcohol is contained in an amount of 1 to 2000 parts by mass inclusive relative to 1 part by mass of hyaluronic acid.

5. The water-soluble hyaluronic acid gel according to any one of items 1 to 4, wherein water is contained in an amount of 700 parts by mass or less relative to 1 part by mass of hyaluronic acid.

6. The water-soluble hyaluronic acid gel according to any one of items 1 to 5, wherein the polyhydric alcohol comprises glycerin and a polyhydric alcohol other than glycerin at a ratio of 30:10 to 4:36 by mass.

7. The water-soluble hyaluronic acid gel according to item 6, wherein an aqueous hyaluronic acid solution has a pH value falling within the range from 4.2 to 5.2, in which the aqueous hyaluronic acid solution is prepared by dissolving the components to be contained in the water-soluble hyaluronic acid gel, except the polyhydric alcohol and water, in water in such a manner that 200 parts by mass of water is contained relative to 1 part by mass of hyaluronic acid contained in the water-soluble hyaluronic acid gel.

8. The water-soluble hyaluronic acid gel according to any one of items 1 to 7, having a sheet-like form.

9. A water-soluble hyaluronic acid gel sheet comprising: a support material; and a water-soluble hyaluronic acid gel as recited in any one of items 1 to 8 which is formed on the support material.

10. A cosmetic comprising a water-soluble hyaluronic acid gel as recited in any one of items 1 to 8.

11. A pharmaceutical composition for external applications, comprising a water-soluble hyaluronic acid gel as recited in any one of items 1 to 8.

12. A composition for medical tools, comprising a water-soluble hyaluronic acid gel as recited in any one of items 1 to 8.

13. A method for producing a water-soluble hyaluronic acid gel, comprising a step of mixing hyaluronic acid, a polyhydric alcohol, an acid, 0 to 10% by mass of a water-soluble organic solvent and water together to prepare a gel-forming aqueous solution (i.e., an aqueous solution for forming a gel).

14. The method for producing a water-soluble hyaluronic acid gel according to item 13, further comprising a step of evaporating water contained in the gel-forming aqueous solution.

15. The method for producing a water-soluble hyaluronic acid gel according to item 14, wherein the evaporation of water is carried out in such a state that the gel-forming aqueous solution is placed in a container.

16. The method for producing a water-soluble hyaluronic acid gel according to item 14 or 15, further comprising a step of adding water after water contained in the gel-forming aqueous solution is evaporated.

17. A method for producing a water-soluble hyaluronic acid gel, comprising: a step of mixing hyaluronic acid, a polyhydric alcohol, 0 to 10% by mass of a water-soluble organic solvent and water together to prepare an aqueous hyaluronic acid solution; and a step of adding an acid to the aqueous hyaluronic acid solution.

18. A method for producing a water-soluble hyaluronic acid gel, comprising: a step of mixing hyaluronic acid, a polyhydric alcohol, 0 to 10% by mass of a water-soluble organic solvent and water together to prepare an aqueous hyaluronic acid solution; a step of drying the aqueous hyaluronic acid solution; and a step of adding an acid to the dried aqueous hyaluronic acid solution.

Advantages of the Invention

According to the present invention, a water-soluble hyaluronic acid gel in which hyaluronic acid is not chemically modified and a large amount of an organic solvent is not contained can be provided. Furthermore, according to the present invention, a method for producing the water-soluble hyaluronic acid gel and a cosmetic, a pharmaceutical composition for external applications or a composition for medical tools each comprising the water-soluble hyaluronic acid gel can also be provided.

EMBODIMENTS OF THE INVENTION

The water-soluble hyaluronic acid gel according to the present invention is characterized by comprising hyaluronic acid, a polyhydric alcohol, an acid and 0 to 10% by mass of a water-soluble organic solvent. Hereinbelow, the water-soluble hyaluronic acid gel, the method for producing the water-soluble hyaluronic acid gel, and the cosmetic, the pharmaceutical composition for external applications or the composition for medical tools each comprising the water-soluble hyaluronic acid gel according to the present invention will be described in detail.

The water-soluble hyaluronic acid gel according to the present invention comprises hyaluronic acid, a polyhydric alcohol, an acid and 0 to 10% by mass of a water-soluble organic solvent. As mentioned below, the water-soluble hyaluronic acid gel according to the present invention can be produced by, for example, preparing a gel-forming aqueous solution comprising hyaluronic acid, a polyhydric alcohol, an acid, 0 to 10% by mass of a water-soluble organic solvent and water and, if necessary, evaporating at least a portion of water from the gel-forming aqueous solution.

In the present invention, the term "hyaluronic acid" is used as a conceptual term that includes hyaluronic acid and a salt thereof within its scope. Therefore, the term "hyaluronic acid and a salt thereof" sometimes simply refers to "hyaluronic acid". The salt of hyaluronic acid is not particularly limited, and examples of the salt include sodium hyaluronate, potassium hyaluronate, magnesium hyaluronate and calcium hyaluronate. In the present invention, hyaluronic acid and the salts thereof may be used singly or two or more of them may be used in combination.

The molecular weight of hyaluronic acid is not particularly limited as long as a gel can be formed. For example, from the viewpoint of the impartment of moderate elasticity, high mechanical strength and a shape retention property to the water-soluble hyaluronic acid gel, the molecular weight is preferably about $5.0 \times 10^4$ to $5.0 \times 10^6$ daltons, more preferably about $1.0 \times 10^5$ to $2.3 \times 10^6$ daltons. Hyaluronic acid having a single molecular weight may be used, or multiple kinds of hyaluronic acid having different molecular weights may be used in combination.

The origin from which hyaluronic acid is derived is not particularly limited. For example, a material isolated/extracted from chicken's comb, umbilical cord or the like, a material prepared by a fermentation method using a microorganism such as a microorganism belonging to the genus *Streptococcus* and the like can be used suitably. In the present invention, a commercially available product of hyaluronic acid may also be used. In the water-soluble hyaluronic acid gel according to the present invention, it is not required to use chemically modified hyaluronic acid. Therefore, the water-soluble hyaluronic acid gel has excellent biocompatibility and can exhibit characteristic properties of natural hyaluronic acid. In other words, in the water-soluble hyaluronic acid gel according to the present invention, only hyaluronic acid that is not substantially chemically modified may be used. The water-soluble hyaluronic acid gel according to the present invention may additionally contain chemically modified hyaluronic acid, as long as the effect of the present invention cannot be inhibited.

Specific examples of the chemically modified hyaluronic acid include hydroxypropyltrimonium hyaluronate, an alkyl (C12-13) glyceryl hydrolyzed hyaluronate, propylene glycol hyaluronate and sodium acetylated hyaluronate. The chemically modified hyaluronic acids may be used singly, or two or more of them may be used in combination.

In the water-soluble hyaluronic acid gel according to the present invention, the content of hyaluronic acid is not particularly limited as long as a gel can be formed. For example, from the viewpoint of the impartment of moderate elasticity, high mechanical strength and a shape retention property to the water-soluble hyaluronic acid gel, the content is about 0.04 to 50% by mass, preferably about 0.06 to 20% by mass, more preferably about 0.2 to 20% by mass. If the content of hyaluronic acid in the water-soluble hyaluronic acid gel is less than 0.04% by mass, a gel may not be formed from a gel-forming aqueous solution as mentioned below. If the content of hyaluronic acid in the water-soluble hyaluronic acid gel is more than 50% by mass, the water-soluble hyaluronic acid gel may become too hard and therefore it may become difficult to use the water-soluble hyaluronic acid gel as a cosmetic, a pharmaceutical composition for external applications, a composition for medical tools or the like as mentioned below.

The acid is not particularly limited, as long as acidic nature can be developed when the acid is mixed with water. The acid may be either an inorganic acid or an organic acid. Examples of the inorganic acid include phosphoric acid, hydrochloric acid, sulfuric acid, nitric acid, perchloric acid and carbonic acid, preferably phosphoric acid, hydrochloric acid and sulfuric acid. Examples of the organic acid include: a monocarboxylic acid such as formic acid, acetic acid, propionic acid, butyric acid, isobutyric acid, valeric acid and lipoic acid; a dicarboxylic acid such as succinic acid, phthalic acid, fumaric acid, oxalic acid, malonic acid and glutaric acid; an oxycarboxylic acid such as glycolic acid, citric acid, lactic acid, pyruvic acid, malic acid, tartaric acid and salicylic acid; a polyhydroxy acid such as glucono-δ-lactone and lactobionic acid; an acidic amino acid such as glutamic acid and aspartic acid; an amino acid derivative such as Nahlsgen (a registered trade name; methyl carboxymethylphenyl aminocarboxypropylphosphonate); and ascorbic acid or a derivative, such as ascorbic acid, ethyl ascorbate and ascorbic acid glucoside. The organic acid is preferably phosphoric acid, ascorbic acid, citric acid, glycolic acid, lactic acid, malic acid, tartaric acid, salicylic acid, ethyl ascorbate, ascorbic acid glucoside, glucono-δ-lactone, lactobionic acid or the like. The acids may be used singly, or two or more of them may be used in combination.

The content of the acid is not particularly limited. The content is preferably chosen in such a manner that an aqueous hyaluronic acid solution can have a pH value falling within the range from 1.9 to 5.2, wherein the aqueous hyaluronic acid solution is prepared by dissolving the components to be contained in the water-soluble hyaluronic acid gel of the present invention, except the polyhydric alcohol and water, in water in such a manner that 200 parts by mass of water is contained relative to 1 part by mass of hyaluronic acid contained in the water-soluble hyaluronic acid gel of the present invention. When the pH value is adjusted to the above-mentioned value, it becomes possible to produce a water-soluble hyaluronic acid gel having moderate elasticity. When the pH value is adjusted to the above-mentioned value, it also becomes possible to produce a water-soluble hyaluronic acid gel having high mechanical strength and a shape retention property. From the same viewpoint, the pH value is more preferably adjusted to a value falling within the range from 2.0 to 4.9. It may be possible to measure the pH value of an aqueous solution of the water-soluble hyaluronic acid gel according to the present invention which also contains the polyhydric alcohol by preparing the aqueous solution in such a manner that 200 parts by mass of water is contained relative to 1 part by mass of hyaluronic acid contained in the water-soluble hyaluronic acid gel of the present invention. However, if the content of the polyhydric alcohol is too much, the pH value cannot be measured accurately. Therefore, it is desirable to measure the pH value in the aforementioned manner.

The polyhydric alcohol is not particularly limited. From such a viewpoint that the polyhydric alcohol cannot chemically modify hyaluronic acid and the aqueous hyaluronic acid solution can be gelatinized properly without using a large amount of an organic solvent, the polyhydric alcohol is preferably a glycerin-type polyhydric alcohol such as glycerin and diglycerin; a propylene glycol-type polyhydric alcohol such as propylene glycol and dipropylene glycol; 1,3-propanediol, butanediol (including 1,3-butanediol and 1,4-butanediol), 1,2-pentanediol, 1,2-hexanediol or 1,2-octanediol; and an ethylene glycol-type polyhydric alcohol such as ethylene glycol, diethylene glycol, triethylene glycol and polyethylene glycol. The polyhydric alcohol is more preferably glycerin, diglycerin, propylene glycol, 1,3-butanediol, polyethylene glycol 200, polyethylene glycol 400, polyethylene glycol 600, 1,3-propanediol, 1,2-pentanediol, 1,2-hexanediol or the like. The polyhydric alcohols may be used singly, or two or more of them may be used in combination.

From such a viewpoint that moderate elasticity, high mechanical strength and a shape retention property can be imparted to the water-soluble hyaluronic acid gel according to the present invention and the water-soluble hyaluronic acid gel can have such weakly acidic nature that the above-mentioned aqueous hyaluronic acid solution can have a pH value of 4.2 or higher, more preferably 4.6 or higher, it is preferred to use multiple types of polyhydric alcohols in combination, and it is more preferred to use glycerin in combination with another type of polyhydric alcohol (a polyhydric alcohol other than glycerin). Specific examples of the above-mentioned other polyhydric alcohol to be used in combination with glycerin include butanediol, polyethylene glycol (e.g., polyethylene glycol 200), propylene glycol, propanediol, diglycerin, pentanediol and hexanediol. The above-mentioned other polyhydric alcohols to be used in combination with glycerin may be used singly, or two or more of them may be used in combination. The water-soluble hyaluronic acid gel which is imparted with moderate elasticity, high mechanical strength and a shape retention property and has such weakly acidic nature that the aqueous hyaluronic acid solution can have a pH value of 4.2 or higher, more preferably 4.6 or higher, is less irritating to skin, has high active ingredient stability, is easy to handle, and is particularly suitable as a cosmetic, a pharmaceutical composition for external applications, a composition for medical tools and the like through which the water-soluble hyaluronic acid gel is in contact with skin directly. In the present invention, the term "moderate elasticity" refers to, for example, such a property that the water-soluble hyaluronic acid gel can snap back moderately upon being pressed with a finger. The term "high mechanical strength" refers to, for example, strength to such an extent that a sheet made from the water-soluble hyaluronic acid gel which has a thickness of about 100 μm cannot be broken even when the sheet is held between fingers and is then pulled up. The term "a shape retention property" refers to such a property that, when the water-soluble hyaluronic acid gel is allowed to stand, the standing shape of the water-soluble hyaluronic acid gel can be retained, unlike a high-viscosity solution.

When glycerin is used in combination with another type of polyhydric alcohol, the content ratio of these components is not particularly limited. From such a viewpoint that the water-soluble hyaluronic acid gel can have moderate elasticity, high mechanical strength and a shape retention property and can also have weakly acidic nature (e.g., the aqueous hyaluronic acid solution can have a pH value of 4.2 or higher), the ratio of the content of glycerin to the content of another polyhydric alcohol (i.e., glycerin:another polyhydric alcohol) is preferably 30:10 by mass to 4:36 by mass, more preferably 25:15 by mass to 4:36 by mass, still more preferably 20:20 by mass to 4:36 by mass, for example.

In the water-soluble hyaluronic acid gel according to the present invention, if it is tried to increase the pH value of the above-mentioned aqueous hyaluronic acid solution, the impartment of moderate elasticity to the water-soluble hyaluronic acid gel generally tends to become difficult. However, when multiple types of polyhydric alcohols are used in combination as mentioned above and hyaluronic acid having a high molecular weight (e.g., a molecular weight of 2000000 or more) is used, even if the pH value of the above-mentioned aqueous hyaluronic acid solution is increased to about 5.2 for example, the water-soluble hyaluronic acid gel can have moderate elasticity and an excellent shape retention property.

The content of the polyhydric alcohol in the water-soluble hyaluronic acid gel according to the present invention is not particularly limited as long as the water-soluble hyaluronic acid gel can have the form of a gel. The content of the polyhydric alcohol is preferably 1 part by mass or more, more preferably about 1 to 2000 parts by mass, still more preferably about 4 to 1500 parts by mass, particularly preferably about 5 to 500 parts by mass. If the content of the polyhydric alcohol is too small, the water-soluble hyaluronic acid gel becomes too hard and consequently it might be difficult to impart moderate elasticity to the water-soluble hyaluronic acid gel. If the content of the polyhydric alcohol is too large, the water-soluble hyaluronic acid gel becomes too soft and consequently it might be difficult to impart sufficient mechanical strength to the water-soluble hyaluronic acid gel. In the water-soluble hyaluronic acid gel according to the present invention, when the polyhydric alcohol is contained in an amount of 500 parts by mass or less relative to 1 part by mass of hyaluronic acid for example, the water-soluble hyaluronic acid gel can have a high shape retention property and moderate elasticity and cannot be broken even when lifted with hands, and can also have sufficient mechanical strength. If the polyhydric alcohol is contained in an amount of more than 500 parts by mass and 1500 parts by mass or less relative to 1 part by mass of hyaluronic acid for example, although the water-soluble hyaluronic acid gel can have a high shape retention property and moderate elasticity, the polyhydric alcohol may bleed out from the water-soluble hyaluronic acid gel and consequently the mechanical property of the water-soluble hyaluronic acid gel may be deteriorated slightly. Furthermore, if the polyhydric alcohol is contained in an amount of more than 1500 parts by mass and 2000 parts by mass or less relative to 1 part by mass of hyaluronic acid for example, although the water-soluble hyaluronic acid gel can have a high shape retention property and moderate elasticity, the polyhydric alcohol may bleed out from the gel and consequently the mechanical strength of the gel may be deteriorated to such an extent that the gel is broken upon being lifted with hands. The content of the polyhydric alcohol can be selected depending on the mechanical strength required for the intended use of the water-soluble hyaluronic acid gel and the like.

The water-soluble hyaluronic acid gel according to the present invention contains 0 to 10% by mass of a water-soluble organic solvent (excluding the above-mentioned polyhydric alcohol). That is, the water-soluble hyaluronic acid gel according to the present invention can contain 10% by mass or less, preferably 5% by mass or less, more preferably 2% by mass or less, of a water-soluble organic solvent. The water-soluble organic solvent is not particularly limited, and examples of the water-soluble organic solvent include ethanol, methanol, isopropanol and acetone. These water-soluble organic solvents may be used singly, or two or more of them may be used in combination. The water-soluble hyaluronic acid gel according to the present invention can be used suitably in the cosmetology field, the medical field and the like, as mentioned below. From these viewpoints, the water-soluble hyaluronic acid gel according to the present invention preferably contains substantially no water-soluble organic solvent. When the water-soluble organic solvent is used, the viscosity of a gel-forming aqueous solution as mentioned below tends to increase and therefore it becomes often difficult to thinly spread the gel-forming aqueous solution on a substrate or the like. Consequently, when the water-soluble organic solvent is used, it often becomes difficult to form the water-soluble hyaluronic acid gel into a sheet-like form by a simple method such as a cast method. From these viewpoints, it is preferred that the water-soluble hyaluronic acid gel according to the present invention contains substantially no water-soluble organic solvent.

The water-soluble hyaluronic acid gel according to the present invention may contain water. The content of water in the water-soluble hyaluronic acid gel according to the present invention is not particularly limited, as long as a gel can be formed. The content of water is, for example, 700 parts by mass or less, preferably 600 parts by mass or less, more preferably 400 parts by mass or less, still more preferably 200 parts by mass or less, particularly preferably 100 parts by mass or less, relative to 1 part by mass of hyaluronic acid. Since the water-soluble hyaluronic acid gel according to the present invention contains a polyhydric alcohol, it is difficult to completely remove water contained in the water-soluble hyaluronic acid gel. Thus, the water-soluble hyaluronic acid gel according to the present invention generally contains water in an amount of 0.02 parts by mass or more relative to 1 part by mass of hyaluronic acid.

The elasticity, the mechanical strength, the shape retention property and the like of the water-soluble hyaluronic acid gel according to the present invention can be adjusted by adjusting the content of each of the components in the water-soluble hyaluronic acid gel, the molecular weight of hyaluronic acid or the range of the pH value of the above-mentioned aqueous hyaluronic acid solution. For example, when the content (content ratio) of hyaluronic acid in the water-soluble hyaluronic acid gel is increased, the water-soluble hyaluronic acid gel tends to become hard and the elasticity, the mechanical strength and the shape retention property of the water-soluble hyaluronic acid gel tend to increase. For example, when the molecular weight of hyaluronic acid in the water-soluble hyaluronic acid gel is increased, the water-soluble hyaluronic acid gel tends to become hard, and the elasticity, the mechanical strength and the shape retention property of the water-soluble hyaluronic acid gel tend to increase. Furthermore, as mentioned above, when multiple types of polyhydric alcohols are used in combination, even if the aqueous hyaluronic acid solution has a pH value of 4.2 or higher, the mechanical strength of the water-soluble hyaluronic acid gel can be improved. On the other hand, when the amounts (content ratios) of the polyhydric alcohol and water in the water-soluble hyaluronic acid gel are increased, the water-soluble hyaluronic acid gel tends to become soft, and the elasticity, the mechanical strength and the shape retention property of the water-soluble hyaluronic acid gel tend to be deteriorated. When the above-mentioned aqueous hyaluronic acid solution has a pH value falling within the range from 1.9 to 5.2, for example, the water-soluble hyaluronic acid gel tends to become hard, and the elasticity, the mechanical strength and the shape retention property of the water-soluble hyaluronic acid gel tend to increase with the decrease in the pH value.

The water-soluble hyaluronic acid gel according to the present invention has water solubility. The water solubility of the water-soluble hyaluronic acid gel according to the present invention refers to a fact that, when a sheet made from the water-soluble hyaluronic acid gel and having a thickness of 100 μm, a length of 4 cm and a width of 4 cm is dissolved completely within 4 hours when the sheet is placed in 100 mL of a phosphate buffer having a pH value of 7.4 and is then stirred at 37° C. at 120 rpm using a stirrer bar.

The shape of the water-soluble hyaluronic acid gel according to the present invention is not particularly limited, and can be chosen properly depending on the intended use. Examples of the shape of the water-soluble hyaluronic acid gel according to the present invention include a sheet-like form, a granular form, and a massive form. For example, when the water-soluble hyaluronic acid gel has a sheet-like form (i.e., a water-soluble hyaluronic acid gel sheet), the water-soluble hyaluronic acid gel according to the present invention can be used suitably as a cosmetic, a pharmaceutical composition for external applications, a composition for medical tools or the like by adhering to skin, as mentioned below. The thickness of the water-soluble hyaluronic acid gel sheet is not particularly limited, and can be, for example, about 0.01 to 10 mm, preferably about 0.05 to 5 mm. For example, when the water-soluble hyaluronic acid gel has a massive form, the water-soluble hyaluronic acid gel can be used suitably as a cosmetic composition for massaging a face or a body, or the like.

Since the water-soluble hyaluronic acid gel according to the present invention contains hyaluronic acid that has a moisturizing effect and the like, the water-soluble hyaluronic acid gel can be applied onto skin in the cosmetology field, the medical field and the like. Specifically, the water-soluble hyaluronic acid gel according to the present invention can be used suitably as a cosmetic, a pharmaceutical composition for external applications, a composition for medical tools or the like. When the water-soluble hyaluronic acid gel according to the present invention is used as a cosmetic, a pharmaceutical composition for external applications or a composition for medical tools, a known component that can be added to a cosmetic, a quasi drug, a medicine or a medical tool can be further added. Examples of the component include skin-whitening components, anti-aging components, oil components, various vitamin components and derivatives thereof, various plant extracts, anti-inflammatory agents, antioxidant agents, dyes, flavoring agents (aroma components) and honey. When a fat-soluble component is added to the water-soluble hyaluronic acid gel according to the present invention, it is possible to add the fat-soluble component in the form of a liposome, an emulsion, a nano-emulsion and the like. These components may be used singly, or two or more of them may be used in combination.

Specific examples of the skin-whitening component include vitamin C or derivatives thereof, and astaxanthin. Specific examples of the anti-aging component include Nahlsgen (a registered trade name; methyl carboxymethylphenyl aminocarboxypropylphosphonate), pyrroloquinoline quinone, LR2412 (a registered trade name; sodium tetrahydrojasmonate) and Green Peel (a registered trade name; a plant essential oil). Specific examples of the oil component include squalane, jojoba oil and olive oil.

In the water-soluble hyaluronic acid gel according to the present invention, a water-soluble polymer such as collagen, porphyrin, acetylglucosamine, hydroxypropyl cellulose, polyvinylpyrrolidone, polyvinyl alcohol, Lipidure (a registered trade name; a homopolymer or copolymer of 2-methacryloyloxyethyl phosphorylcholine), hyaluronic acid having a low molecular weight, e.g., 10000 or less, or a salt of hyaluronic acid may be added. These water-soluble polymers may be used singly, or two or more of them may be used in combination.

The water-soluble hyaluronic acid gel according to the present invention can be imparted with moderate elasticity, moderate mechanical strength and a moderate shape retention property, and therefore the water-soluble hyaluronic acid gel according to the present invention can be used as-is as a facial pack. When the water-soluble hyaluronic acid gel according to the present invention is used as a facial pack, it is preferred that the water-soluble hyaluronic acid gel according to the present invention is in a sheet-like form.

When used as a facial pack, the water-soluble hyaluronic acid gel according to the present invention sheet is adhered onto skin directly and then held on the skin for a certain time of period. In this manner, the moisturizing effect of hyaluronic acid or the like can be imparted to the skin. When the water-soluble hyaluronic acid gel according to the present invention contains a known component that can be added to a cosmetic, a quasi drug, a medicine or a medical tool as mentioned above, the component can be absorbed transdermally by adhering the water-soluble hyaluronic acid gel according to the present invention sheet onto skin directly.

For example, when salicylic acid is used as the acid in the water-soluble hyaluronic acid gel according to the present invention, since salicylic acid has an effect of softening cuticles in skin, the water-soluble hyaluronic acid gel can be used suitably as a cosmetic, a quasi drug, a medicine or the like for caring for a body part in which cuticles in skin are tend to be thickened (e.g., joints, heels, and corns and calluses on foot soles) by adhering a sheet made from the water-soluble hyaluronic acid gel according to the present invention made into a sheet-like form onto the skin. When the salicylic acid-containing water-soluble hyaluronic acid gel is used in the above-mentioned use applications, the time of use of the water-soluble hyaluronic acid gel becomes relatively long. Therefore, in this case, it is preferred that the water-soluble hyaluronic acid gel is used in combination with a support material, an adhesive tape or the like as mentioned below. In this regard, since salicylic acid is poorly soluble in water, undissolved crystals of salicylic acid exist in the water-soluble hyaluronic acid gel according to the present invention when salicylic acid is dissolved at a high concentration. However, even when the crystals exist in the water-soluble hyaluronic acid gel, the water-soluble hyaluronic acid gel can still be used suitably in the above-mentioned use applications.

Since the water-soluble hyaluronic acid gel according to the present invention is soluble in water, hyaluronic acid can be eluted from the water-soluble hyaluronic acid gel into water easily. Therefore, the water-soluble hyaluronic acid gel according to the present invention can highly exhibit the effect of hyaluronic acid contained therein, i.e., impartment of moistness and springiness to skin, when applied onto skin, and therefore can be used suitably in the cosmetology field and the like. For example, the moisturizing effect of hyaluronic acid eluting into water can be further increased by adhering the water-soluble hyaluronic acid gel according to the present invention sheet onto skin and then massaging the skin while applying water to the sheet to gradually dissolve the sheet.

Furthermore, since the water-soluble hyaluronic acid gel according to the present invention has excellent biocompatibility and also has a high water-absorbing/moisturizing effect, the water-soluble hyaluronic acid gel is suitable for use at wound areas or in medical tools for protecting pressure sore areas or the like. For example, since the water-soluble hyaluronic acid gel according to the present invention has excellent biocompatibility and also has a high water-absorbing/moisturizing effect, the water-soluble hyaluronic acid gel can be used suitably as a pad in a first-aid adhesive tape, a material for covering and protecting pressure sore areas or the like. When the water-soluble hyaluronic acid gel is used in these use applications, a healing acceleration component such as an epithelial growth factor or an anti-bacterial component can be added to the water-soluble hyaluronic acid gel.

The water-soluble hyaluronic acid gel according to the present invention may be arranged on a support material upon use. By forming the water-soluble hyaluronic acid gel on a support material, a water-soluble hyaluronic acid gel sheet can be produced conveniently. The support material is not particularly limited, and examples include a non-woven fabric, a woven fabric, a woven material, paper and a polymer film (a film of a polyolefin such as polyethylene terephthalate and polyethylene, vinyl chloride, polyurethane and the like). More preferably, from the viewpoint of the strength of adhesion between the water-soluble hyaluronic acid gel and the support material, the support material is a laminate film made from a non-woven fabric and a polymer film or a non-woven fabric. Alternatively, for the purpose of holding the water-soluble hyaluronic acid gel arranged on a support material on skin, the water-soluble hyaluronic acid gel may be fixed with an adhesive tape, a hydrogel tape, a supporter, a bandage, a mask, an eye mask or the like.

The water-soluble hyaluronic acid gel according to the present invention itself can be provided as a product without requiring any modification. Alternatively, the gel may be integrated with an adhesive tape, a support material or the like to form a product, or the water-soluble hyaluronic acid gel itself may be provided as a product which is to be fixed with an adhesive tape, a hydrogel tape, a supporter, a bandage, a mask, an eye mask or the like upon use.

The method for producing the water-soluble hyaluronic acid gel according to the present invention is not particularly limited. For example, a method comprising a step of mixing hyaluronic acid, the polyhydric alcohol, the acid, 0 to 10% by mass of the water-soluble organic solvent and water together to prepare a gel-forming aqueous solution can be mentioned. In the method for producing the water-soluble hyaluronic acid gel according to the present invention, the order of mixing the components is not particularly limited. The method for mixing the components is not particularly limited, either. For example, the components can be mixed using a stirrer or the like.

In the method for producing the water-soluble hyaluronic acid gel according to the present invention, it is preferred that the pH value of an aqueous hyaluronic acid solution prepared by mixing hyaluronic acid, the acid, 0 to 10% by mass of the water-soluble organic solvent and water together is adjusted to a value mentioned below. That is, for the preparation of the gel-forming aqueous solution, it is preferred to firstly prepare the aqueous hyaluronic acid solution by dissolving the components to be contained in the water-soluble hyaluronic acid gel, except the polyhydric alcohol and water, in water, and then adjust the amount of the acid in such a manner that the aqueous hyaluronic acid solution in which the amount of water is 200 parts by mass relative to 1 part by mass of hyaluronic acid can have a pH value falling within the range from about 1.9 to 5.2. When the pH value is adjusted to the above-mentioned value, the water-soluble hyaluronic acid gel can be produced conveniently without requiring any chemical modification of hyaluronic acid or without requiring the use of a large amount of the organic solvent for causing gelatinization. The pH value is preferably about 2.0 to 4.9.

The amount of water in the gel-forming aqueous solution is not particularly limited. For example, the amount of water is about 5 to 1000 parts by mass, preferably about 20 to 400 parts by mass, relative to 1 part by mass of hyaluronic acid. If the amount of water in the gel-forming aqueous solution is too small, the viscosity of the gel-forming aqueous solution becomes too high and it sometimes becomes difficult to mix hyaluronic acid, the polyhydric alcohol, the acid and 0 to 10% by mass of the water-soluble organic solvent in water homogenously. On the contrary, if the amount of water is too large, it is required to remove a large amount of water from the gel-forming aqueous solution for causing the gelatinization of the gel-forming aqueous solution.

In the method for producing the water-soluble hyaluronic acid gel according to the present invention, for the purpose of gelatinizing the above-mentioned gel-forming aqueous solution, or increasing the elasticity of the water-soluble hyaluronic acid gel or the like, a step of evaporating at least a portion of water contained in the gel-forming aqueous solution may be additionally involved. The elasticity of the water-soluble hyaluronic acid gel according to the present invention can be adjusted properly depending on the intended use. Therefore, when the water-soluble hyaluronic acid gel according to the present invention is to be used in an extremely soft state for example, it is only needed to properly adjust the contents of the components, the pH value of the aqueous hyaluronic acid solution or the like, whereby the gel-forming aqueous solution can be used as the water-soluble hyaluronic acid gel according to the present invention without requiring the evaporation of water from the gel-forming aqueous solution. Alternatively, the elasticity, the mechanical strength and the shape retention property of the water-soluble hyaluronic acid gel may also be improved by evaporating at least a portion of water from the gel-forming aqueous solution. From the viewpoint of the improvement in the elasticity, the mechanical strength and the shape retention property of the water-soluble hyaluronic acid gel and from the viewpoint of the management of the quality of the gel, it is preferred to evaporate a large portion of water from the gel-forming aqueous solution.

The method for evaporating water from the gel-forming aqueous solution is not particularly limited. For example, a method of heating the gel-forming aqueous solution to dryness using a drying machine such as a thermostatic bath, a method of heating the gel-forming aqueous solution to dryness by applying warm air to the gel-forming aqueous solution, and a method of heating the gel-forming aqueous solution to dryness on an electric griddle can be mentioned. For example, when it is intended to form a sheet of the water-soluble hyaluronic acid gel according to the present invention, the water-soluble hyaluronic acid gel sheet can be produced easily by spreading the gel-forming aqueous solution on a base plate such as a polyethylene terephthalate film at a uniform thickness and then heating the spread gel-forming aqueous solution to dryness (a cast method).

Alternatively, the water-soluble hyaluronic acid gel sheet can also be produced easily by: placing the gel-forming aqueous solution in a container, e.g., a tray and a dish, in such a manner that the gel can have a predetermined thickness; and then drying the gel-forming aqueous solution in a drying machine, e.g., a thermostatic bath (a batch method). That is, when the gel-forming aqueous solution is placed in a container and then water is evaporated from the gel-forming aqueous solution, a water-soluble hyaluronic acid gel sheet formed in the container can be provided as a whole as a final product. In this case, a processing step such as a step of cutting the water-soluble hyaluronic acid gel sheet can be eliminated.

In the method for producing the water-soluble hyaluronic acid gel according to the present invention, it may also be possible to add water after the preparation of the water-soluble hyaluronic acid gel. For example, it may be possible to carry out a step of adding water after the evaporation of water contained in the gel-forming aqueous solution. In particular, a water-soluble hyaluronic acid gel having a properly controlled water content can be produced by evaporating a large portion of water contained in the gel-forming aqueous solution to form a water-soluble hyaluronic acid gel and then carrying out a step of adding water to the water-soluble hyaluronic acid gel. In the step of adding water, the above-mentioned components may be added easily. When a thermally unstable component or a volatile component is to be added to the gel, the content of the component in the gel can be controlled properly by adding the component together with water after the drying step.

Furthermore, in the method for producing the water-soluble hyaluronic acid gel according to the present invention, when the above-mentioned known component which can be added to a cosmetic, a quasi drug, a medicine and a medical tool is further added for example, it may be possible to add the component after the water-soluble hyaluronic acid gel is prepared.

In the method for producing the water-soluble hyaluronic acid gel according to the present invention, the contents of hyaluronic acid, the polyhydric alcohol, the acid and the water-soluble organic solvent in the gel-forming aqueous solution can be selected in such a manner that the above-mentioned contents of these components can be achieved in the finished water-soluble hyaluronic acid gel.

As another example of the method for producing the water-soluble hyaluronic acid gel according to the present invention, a method can be mentioned, which comprises a step of mixing hyaluronic acid, the polyhydric alcohol, 0 to 10% by mass of the water-soluble organic solvent and water together to prepare an aqueous hyaluronic acid solution and a step of adding the acid to the aqueous hyaluronic acid solution. The method for adding the acid is not particularly limited. For example, a method of carrying out the spraying, application or the like of a solution containing the acid onto the aqueous hyaluronic acid solution can be employed. According to this addition method, the acid can be added uniformly to the aqueous hyaluronic acid solution that has been spread in the form of a sheet. Therefore, the method is suitable for producing a hyaluronic acid gel having a sheet-like form. When this production method is employed, the same amounts of hyaluronic acid, the polyhydric alcohol, 0 to 10% by mass of the water-soluble organic solvent and water as those mentioned above can be employed. The method for evaporating water can also be carried out in the same manner as mentioned above.

As still another example of the method for producing the water-soluble hyaluronic acid gel according to the present invention, a method can be mentioned, which comprises a step of mixing hyaluronic acid, the polyhydric alcohol, 0 to 10% by mass of the water-soluble organic solvent and water together to prepare an aqueous hyaluronic acid solution, a step of drying the aqueous hyaluronic acid solution, and a step of adding the acid to the dried aqueous hyaluronic acid solution. For example, in a case where a thermally unstable acid or a volatile acid is used, the content of the acid in the gel can be controlled preferably by adding the acid after the drying step. When the component is to be contained in the gel, the content of the component in the gel can be controlled properly by adding the thermally unstable component or the volatile component in the acid addition step after the drying step. In addition, it is also possible to add water in the acid addition step. A water-soluble hyaluronic acid gel having a properly controlled acid content and a properly controlled water content can be produced by carrying out a step of adding water together with the acid after a large portion of water contained in the aqueous hyaluronic acid solution is evaporated.

When the water-soluble hyaluronic acid gel according to the present invention is to be produced in a massive form, the water-soluble hyaluronic acid gel having a massive form may be produced by, for example, immersing an aqueous hyaluronic acid solution, which is a solution prepared by mixing hyaluronic acid, the polyhydric alcohol, 0 to 10% by mass of the water-soluble organic solvent and water together, in a solution containing the acid. From the viewpoint of the easiness of the production of the water-soluble hyaluronic acid gel according to the present invention in a massive form, it is preferred to further add a polyhydric alcohol to the solution containing the acid.

In the method for producing the water-soluble hyaluronic acid gel according to the present invention, the contents of hyaluronic acid, the polyhydric alcohol and the water-soluble organic solvent in the aqueous hyaluronic acid solution and the amount of the acid to be added can be adjusted so that the above-mentioned contents of these components can be achieved in the finished water-soluble hyaluronic acid gel.

EXAMPLES

The present invention will be described in detail with reference to Examples and Comparative Examples. However, the present invention is not limited to these examples. The reagents used in the below-mentioned Examples and Comparative Examples are mentioned below. Each of the compositions shown in Tables is expressed in the unit "part(s) by mass".

<Reagents>

Hyaluronic acid (1600000): sodium hyaluronate, a product name "HYALURONIC ACID HA-LQH" (product labeling: a molecular weight of 120 to 2200000; an average molecular weight of 1600000) manufactured by Kewpie Corporation Hyaluronic acid (300000): hyaluronic acid, a product name "HYALURONIC ACID HA-LF-P" (product labeling: a molecular weight of 200000 to 500000; an average molecular weight of 300000) manufactured by Kewpie Corporation Hyaluronic acid (2300000): sodium hyaluronate, a product name "HYALURONSAN HA-LQSH" (product labeling: a molecular weight of 1600000 to 2900000, average molecular weight 2300000) manufactured by Kewpie Corporation Hyaluronic acid (100000): sodium hyaluronate, a product name "hyaluronic acid FCH-SU" (product labeling: an average molecular weight of 50000 to 110000) manufactured by Kikkoman Biochemifa Company Glycerin: glycerin manufactured by Wako Pure Chemical Industries, Ltd. (Special Grade)

Propylene glycol: propylene glycol manufactured by Wako Pure Chemical Industries, Ltd. (Special Grade)

Butanediol: 1,3-butanediol manufactured by Wako Pure Chemical Industries, Ltd. (Special Grade)

PEG 200: polyethylene glycol 200 manufactured by Wako Pure Chemical Industries, Ltd. (1st Grade)

Propanediol: 1,3-propanediol manufactured by Wako Pure Chemical Industries, Ltd. (Special Grade)

Diglycerin: diglycerin manufactured by Wako Pure Chemical Industries, Ltd. (for gas chromatography)

Pentanediol: 1,2-pentanediol manufactured by Wako Pure Chemical Industries, Ltd.

Hexanediol: 1,2-hexanediol manufactured by Wako Pure Chemical Industries, Ltd.

10% Phosphoric acid: phosphoric acid manufactured by Wako Pure Chemical Industries, Ltd. (Special Grade)

2% Sulfuric acid: sulfuric acid manufactured by Wako Pure Chemical Industries, Ltd. (Special Grade)

2% Hydrochloric acid: hydrochloric acid manufactured by Wako Pure Chemical Industries, Ltd. (Special Grade)

Vitamin C: L(+)-ascorbic acid manufactured by Wako Pure Chemical Industries, Ltd. (Special Grade)

Acetic acid: acetic acid manufactured by Nacalai Tesque Inc. (for column chromatography)

Citric acid: citric acid monohydrate manufactured by Wako Pure Chemical Industries, Ltd. (Special Grade)

Salicylic acid: salicylic acid manufactured by Wako Pure Chemical Industries, Ltd. (Special Grade)

Ethyl ascorbic acid: a product name "VC ethyl" manufactured by Nippon Fine Chemical Co., Ltd.

Gluconolactone: glucono-δ-lactone manufactured by Wako Pure Chemical Industries, Ltd. (Japanese Pharmaceutical Excipients)

Lactobionic acid: lactobionic acid manufactured by Wako Pure Chemical Industries, Ltd. (1st Grade)

Aspartic acid: DL-aspartic acid manufactured by Wako Pure Chemical Industries, Ltd. (Special Grade)

Collagen: a water-soluble collagen solution, a product name "Collagen P (PF)" manufactured by Nitta Gelatin Inc.

Hyaluronic acid (10000): hydrolyzed hyaluronic acid, a product name "Hiaroorigo" (product labeling: a molecular weight of 10000 or less) manufactured by Kewpie Corporation Hyalorepair: hydrolyzed hyaluronic acid alkyl (C12-13) glyceryl, a product name "Hyalorepair" manufactured by Kewpie Corporation Honey: purified honey manufactured by API Co., Ltd.

Examples 1 to 15 and Comparative Example 1

Hyaluronic acid (sodium hyaluronate), an acid and distilled water were mixed together using a propeller-type rotary stirrer at mixing ratios (part(s) by mass) shown in Table 1. In this manner, aqueous hyaluronic acid solutions were prepared. The pH values of the resultant aqueous hyaluronic acid solutions were measured using TwinpH (B-212) manufactured by Horiba Ltd. The results are shown in Table 1. A polyhydric alcohol (glycerin) was added to each of the aqueous hyaluronic acid solutions at a mixing ratio (parts by mass) shown in Table 1, and the resultant mixture was agitated using a propeller-type rotary stirrer. In this manner, gel-forming aqueous solutions were prepared. Subsequently, each of the gel-forming aqueous solutions was applied at a uniform thickness onto a polyethylene terephthalate film having a thickness of 50 μm, and then dried on an electric griddle at 90° C. for 3 hours to evaporate a large portion of distilled water. In this manner, hyaluronic acid gel sheets each having a thickness of about 100 μm were produced. In Comparative Example 1, a sheet was produced in the same manner as in Examples 1 to 15, except that no acid was added. In Comparative Example 1, however, when a gel-forming aqueous solution was dried, a gel was not formed but a highly viscous solution was produced instead. For reference, a gel-forming aqueous solution prepared in Example 4 for the production of a hyaluronic acid gel sheet and a dried hyaluronic acid gel sheet produced in Example 4 were weighed, and the weights are as follows.

The weight of the gel-forming aqueous solution: 4.10 g (solid content: 0.70 g)
The weight of hyaluronic acid gel sheet: 0.71 g
In this regard, the solid content in the gel-forming aqueous solution refers to the total amount of the components used for the preparation of the gel-forming aqueous solution except distilled water.

<Evaluation of Properties of Hyaluronic Acid Gel Sheet>

The hyaluronic acid gel sheets produced in Examples 1 to 15 and the sheet-like highly viscous solution produced in Comparative Example 1 were evaluated on the basis of the criteria shown below. The results are shown in Table 1.
0: A gel which was colorless, transparent and slightly hard and had a high shape retention property.
1: A gel which was colorless and transparent, had moderate elasticity, and also had a high shape retention property.
2: A gel which was colorless, transparent and soft, and had a slightly high shape retention property.
3: A gel which was colorless, transparent and considerably soft, and had a poor shape retention property.
4: A colorless, transparent and highly viscous solution.

<Test on Solubility of Hyaluronic Acid Gel>

Each of the hyaluronic acid gel sheets (4 cm×4 cm) produced in Examples 4, 6, 10 and 12 was placed in a phosphate buffer solution (100 mL) having a pH value of 7.4, and then stirred at 37° C. at 120 rpm for 4 hours using a stirrer bar. As a result, all of the hyaluronic acid gel sheets were dissolved completely, and therefore it was confirmed that the hyaluronic acid gel sheets were water-soluble.

<Comparison of pH Value of Gel-Forming Aqueous Solution with pH Value of Aqueous Solution Prepared by Dissolving Hyaluronic Acid Gel Sheet in Distilled Water>

The pH values of the gel-forming aqueous solutions prepared in Examples 3, 5 and 7 were measured using TwinpH (B-212) manufactured by Horiba Ltd. The results are shown in Table 2. Subsequently, distilled water was added to each of the hyaluronic acid gel sheets produced in Examples 3, 5 and 7 in such a manner that the aqueous solution had the same composition as that of the corresponding gel-forming aqueous solution. In this manner, aqueous solutions were prepared. The pH values of the aqueous solutions were measured using TwinpH (B-212) manufactured by Horiba Ltd. The results are shown in Table 2. The amounts of water added were 199 parts by mass in Example 3, 198 parts by mass in Example 5 and 190 parts by mass in Example 7 relative to 1 part by mass of hyaluronic acid contained in each of the hyaluronic acid gel sheets.

TABLE 1

| | Composition of gel-forming aqueous solution | Example 1 | Example 2 | Example 3 | Example 4 | Example 5 | Example 6 | Example 7 | Example 8 |
|---|---|---|---|---|---|---|---|---|---|
| | Hyaluronic acid (1600000) | 1 | 1 | 1 | 1 | 1 | 1 | 1 | 1 |
| | Glycerin | 40 | 40 | 40 | 40 | 40 | 40 | 40 | 40 |
| Acid | 10% Phosphoric acid | 0.25 | 0.50 | 0.75 | 1.00 | 2.00 | 5.00 | 10.00 | 15.00 |
| | 2% Sulfuric acid | | | | | | | | |
| | 2% Hydrochloric acid | | | | | | | | |
| | Vitamin C | | | | | | | | |
| | Acetic acid | | | | | | | | |
| | Distilled water | 200 | 199 | 199 | 199 | 198 | 195 | 190 | 185 |
| | PH of aqueous hyaluronic acid solution | 4.6 | 4.0 | 3.8 | 3.7 | 3.1 | 2.5 | 2.1 | 2.0 |
| | Type of sheet | 3 | 3 | 1 | 1 | 1 | 1 | 1 | 2 |

| | Composition of gel-forming aqueous solution | Example 9 | Example 10 | Example 11 | Example 12 | Example 13 | Example 14 | Example 15 | Comparative Example 1 |
|---|---|---|---|---|---|---|---|---|---|
| | Hyaluronic acid (1600000) | 1 | 1 | 1 | 1 | 1 | 1 | 1 | 1 |
| | Glycerin | 40 | 40 | 40 | 40 | 40 | 40 | 40 | 40 |
| Acid | 10% Phosphoric acid | | | | | | | | |
| | 2% Sulfuric acid | 5 | | | | | | | |
| | 2% Hydrochloric acid | | 5 | | | | | | |
| | Vitamin C | | | 1 | 10 | 20 | | | |
| | Acetic acid | | | | | | 5 | | |
| | Citric acid | | | | | | | 1 | |
| | Distilled water | 195 | 195 | 199 | 190 | 180 | 195 | 199 | 200 |
| | PH of aqueous hyaluronic acid solution | 2.8 | 3.5 | 3.6 | 2.8 | 2.5 | 3.0 | 2.8 | 6.7 |
| | Type of sheet | 1 | 1 | 2 | 1 | 1 | 2 | 1 | 4 |

From the results shown in Table 1, it is found that hyaluronic acid gel sheets were produced in Examples 1 to 15 in each of which hyaluronic acid, glycerin, an acid and distilled water were used. It is also found that, when the pH value of an aqueous hyaluronic acid solution, which is a solution prepared by mixing hyaluronic acid, the acid and distilled water together, is adjusted to a value falling within the range from 2.0 to 3.8 in the process of preparing the hyaluronic acid gel sheet, the gel sheet can be used particularly suitably as a cosmetic, a pharmaceutical composition for external applications or a composition for medical tools from the viewpoint of elasticity and the shape retention property. In contrast, in Comparative Example 1 in which no acid was used, a gel was not produced but a highly viscous solution was produced instead.

TABLE 2

| | Example 3 | Example 5 | Example 7 |
|---|---|---|---|
| pH of gel-forming aqueous solution | 3.7 | 2.9 | 1.9 |
| pH of aqueous solution prepared by dissolving water-soluble hyaluronic acid gel in distilled water | 3.8 | 3.0 | 2.1 |

As shown in Table 2, the pH value of each of the gel-forming aqueous solutions and the pH value of an aqueous solution, which was a solution produced by dissolving a water-soluble hyaluronic acid gel prepared from the gel-forming aqueous solution in distilled water, were almost the same as each other.

Examples 16 to 20 and Comparative Example 2

Hyaluronic acid gel sheets were produced in the same manner as in Examples 1 to 15, except that hyaluronic acid (molecular weight: 300000) was used in place of sodium hyaluronate (molecular weight: 1600000) and that hyaluronic acid, glycerin, an acid and distilled water were mixed together using a propeller-type rotary stirrer at a mixing ratio (part(s) by mass) shown in Table 3. In Comparative Example 2, a sheet was produced in the same manner as in Examples 16 to 20, except that no acid was added.

Subsequently, the properties of the hyaluronic acid gel sheets produced in Examples 16 to 20 and a sheet-like highly viscous solution produced in Comparative Example 2 were evaluated in the same manner as in Examples 1 to 15. As another evaluation, pH values of aqueous hyaluronic acid solutions, each of which contained the same amounts of hyaluronic acid, distilled water, 10% phosphoric acid and vitamin C as those in Examples 1 to 15 but did not contain glycerin, were measured in the same manner as in Examples 1 to 15. The results are shown in Table 3.

TABLE 3

| Composition of gel-forming aqueous solution | | Example 16 | Example 17 | Example 18 | Example 19 | Example 20 | Comparative Example 2 |
|---|---|---|---|---|---|---|---|
| Hyaluronic acid (300000) | | 1 | 1 | 1 | 1 | 1 | 1 |
| Glycerin | | 40 | 40 | 40 | 40 | 40 | 40 |
| Acid | 10% Phosphoric acid | 1.00 | 5.00 | 10.00 | | | |
| | Vitamin C | | | | 5 | 10 | |
| Distilled water | | 200 | 200 | 200 | 200 | 200 | 200 |
| PH of aqueous hyaluronic acid solution | | 3.7 | 2.5 | 2.1 | 3.1 | 2.9 | 6.3 |
| Type of sheet | | 2 | 1 | 1 | 1 | 1 | 4 |

From the results shown in Table 3, it is found that, in Examples 16 to 20 in which hyaluronic acid was used in place of sodium hyaluronate, as in the case of Examples 1 to 15, hyaluronic acid gel sheet were produced from gel-forming aqueous solutions each produced by mixing hyaluronic acid, glycerin, an acid and distilled water together. In contrast, in Comparative Example 2 in which no acid was added, as in the case of Comparative Example 1, a gel was not produced but a highly viscous solution was produced instead.

Each of the hyaluronic acid gels produced in Examples 17 and 20 was tested with respect to solubility in a phosphate buffer solution in the same manner as in Examples 4, 6, 10 and 12. As a result, both of the hyaluronic acid gel sheets were dissolved completely, and therefore it was confirmed that the hyaluronic acid gel sheets were water-soluble.

Examples 21 to 25

Hyaluronic acid gel sheets of Examples 21 to 25 were produced in the same manner as in Examples 1 to 15, except that glycerin was added at the mixing ratios (part(s) by mass) shown in Table 4. Subsequently, the properties of the hyaluronic acid gel sheets produced in Examples 21 to 25 were evaluated in the same manner as in Examples 1 to 15. The results are shown in Table 4.

TABLE 4

| Composition of gel-forming aqueous solution | Example 21 | Example 22 | Example 23 | Example 24 | Example 25 |
|---|---|---|---|---|---|
| Hyaluronic acid (1600000) | 1 | 1 | 1 | 1 | 1 |
| Glycerin | 1 | 5 | 10 | 50 | 100 |
| 10% Phosphoric acid | 1.00 | 1.00 | 1.00 | 1.00 | 1.00 |
| Distilled water | 200 | 200 | 200 | 200 | 200 |
| Type of sheet | 0 | 1 | 1 | 1 | 3 |

From the results shown in Table 4, it is found that a hyaluronic acid gel sheet can be produced even when glycerin was added in an amount of 1 to 100 parts by mass relative to 1 part by mass of hyaluronic acid.

The hyaluronic acid gel produced in Example 23 was tested with respect to solubility in a phosphate buffer solution in the same manner as in Examples 4, 6, 10 and 12. As a result, the hyaluronic acid gel sheets were dissolved completely, and therefore it was confirmed that the hyaluronic acid gel sheets were water-soluble. For reference, the gel-forming aqueous solutions used for producing the hyaluronic acid gel sheets of Examples 23 and 25 and the hyaluronic acid gel sheets which had been dried were weighed. The weights are as follows.

Example 23

The weight of the gel-forming aqueous solution: 13.12 g (solid content: 0.70 g)
The weight of the hyaluronic acid gel sheet: 0.70 g Example 25

The weight of the gel-forming aqueous solution: 2.09 g (solid content: 0.70 g)
The weight of the hyaluronic acid gel sheet: 0.75 g In this regard, the solid content in each of the gel-forming aqueous solutions refers to the total amount of the components used for the preparation of each of the gel-forming aqueous solutions except distilled water.

Examples 26 to 37

Water-soluble hyaluronic acid gel sheets of Examples 26 to 37 were produced in the same manner as in Examples 1 to 15, except that polyhydric alcohols shown in Table 5 were used at the mixing ratios (part(s) by mass) shown in Table 5 in place of glycerin. Subsequently, the properties of the water-soluble hyaluronic acid gel sheets produced in Examples 26 to 37 were evaluated in the same manner as in Examples 1 to 15. The results are shown in Table 5.

TABLE 5

| Composition of gel-forming aqueous solution | | Example 26 | Example 27 | Example 28 | Example 29 | Example 30 | Example 31 |
|---|---|---|---|---|---|---|---|
| | Hyaluronic acid (1600000) | 1 | 1 | 1 | 1 | 1 | 1 |
| Polyhydric alcohol | Propylene glycol | 5 | 10 | 20 | 40 | | |
| | Butanediol | | | | | 5 | 10 |
| | PEG200 | | | | | | |
| Acid | 10% Phosphoric acid | 1.00 | 1.00 | 1.00 | 1.00 | 1.00 | 1.00 |
| | Distilled water | 200 | 200 | 200 | 200 | 200 | 200 |
| | Type of sheet | 1 | 1 | 1 | 1 | 0 | 0 |

| Composition of gel-forming aqueous solution | | Example 32 | Example 33 | Example 34 | Example 35 | Example 36 | Example 37 |
|---|---|---|---|---|---|---|---|
| | Hyaluronic acid (1600000) | 1 | 1 | 1 | 1 | 1 | 1 |
| Polyhydric alcohol | Propylene glycol | | | | | | |
| | Butanediol | 20 | 40 | | | | |
| | PEG200 | | | 5 | 10 | 20 | 40 |
| Acid | 10% Phosphoric acid | 1.00 | 1.00 | 1.00 | 1.00 | 1.00 | 1.00 |
| | Distilled water | 200 | 200 | 200 | 200 | 200 | 200 |
| | Type of sheet | 1 | 1 | 1 | 1 | 1 | 1 |

From the results shown in Table 5, it is found that a water-soluble hyaluronic acid gel can be produced when propylene glycol, butanediol or polyethylene glycol is used as another polyhydric alcohol in place of glycerin.

The hyaluronic acid gels produced in Examples 29, 33 and 37 were tested with respect to solubility in a phosphate buffer solution in the same manner as in Examples 4, 6, 10 and 12. As a result, all of the hyaluronic acid gel sheets were dissolved completely and therefore it was confirmed that the hyaluronic acid gel sheets were water-soluble.

<Evaluation of Moisturizing Effect of Hyaluronic Acid Gel Sheets by Patch Test>

Each of the hyaluronic acid gel sheets (2 cm×2 cm) produced in Example 4 and Example 16 was adhered for 30 minutes onto a right forearm area of each of six volunteers (A to F) twice (morning and evening) per day. Subsequently, purified water (about 10 mL) was added in portions onto the gel, and the gel was dissolved while massaging for about 3 minutes, fully washed with purified water, and then dried with air. This procedure was carried out continuously for 7 days, and the moisture content in skin was measured in the morning on the day following the last day (i.e., the morning of day 8 after the start of the treatment) using a mobile controller MSC100/corneometer CM825 (Integral Corporation). As a control for comparison, the moisture amount in skin was measured in an untreated left forearm area in the same volunteer. The increase rate (%) of the moisture amount in skin in the right forearm area, to which each of the hyaluronic acid gels was applied, relative to that in the left forearm area in the individual volunteers and an average±SD are shown in Table 6.

TABLE 6

| | Rate of increase in moisture amount in skin (%) | |
|---|---|---|
| Volunteer | Example 4 | Example 16 |
| A | 127 | 133 |
| B | 116 | 113 |
| C | 134 | 141 |
| D | 106 | 135 |
| E | 129 | 122 |
| F | 137 | 123 |
| Average ± SD | 125 ± 12 | 128 ± 10 |

As shown in Table 6, in the hyaluronic acid gel sheets produced in Example 4 and Example 16, a significant effect of increasing the moisture amount in skin relative to that in the case where the skin was untreated. The hyaluronic acid gel sheets had moderate elasticity, also had an excellent shape retention property and therefore were easy to handle, and did not cause a problem such as skin irritation.

Examples 32 to 33

Hyaluronic acid gel sheets of Examples 32 to 33 were produced in the same manner as in Examples 1 to 15, except that salicylic acid was used as an acid as shown in Table 7. Subsequently, the properties of the hyaluronic acid gel sheets produced in Examples 32 to 33 were evaluated in the same manner as in Examples 1 to 15. As another evaluation, pH values of aqueous hyaluronic acid solutions, each of which contained the same amounts of hyaluronic acid, distilled water, and salicylic acid as those in Examples 1 to 15 but did not contain glycerin, were measured in the same manner as in Examples 1 to 15. The results are shown in Table 7. In Example 33, crystals of salicylic acid were contained both in the gel-forming aqueous solution and the hyaluronic acid gel sheet.

TABLE 7

| Composition of gel-forming aqueous solution | Example 32 | Example 33 |
|---|---|---|
| Hyaluronic acid (1600000) | 1 | 1 |
| Glycerin | 40 | 40 |
| Salicylic acid | 0.2 | 4 |
| Distilled water | 200 | 200 |
| PH of aqueous hyaluronic acid solution | 3.4 | 2.8 |
| Type of sheet | 1 | 1 |

Examples 34 to 35

Hyaluronic acid, glycerin and distilled water were placed in a plastic petri dish (diameter: 9 cm) in such a manner that these components were mixed at mixing ratios (part(s) by mass) shown in Table 8, thereby producing homogeneous and highly viscous aqueous hyaluronic acid solutions each having a thickness of about 200 μm. 10% Phosphoric acid was sprayed onto the surface of each of the aqueous hyaluronic acid solutions in an amount that corresponds to the mixing amount (part by mass) shown in Table 8. Subsequently, each of the aqueous hyaluronic acid solution was stored at room temperature for 24 hours, thereby producing a hyaluronic acid gel sheet having a thickness of about 200 μm. Subsequently, the properties of the hyaluronic acid gel sheets produced in Examples 34 to 35 were evaluated in the same manner as in Examples 1 to 15. The results are shown in Table 8.

TABLE 8

| Composition of gel-forming aqueous solution | Example 34 | Example 35 |
|---|---|---|
| Hyaluronic acid (1600000) | 1 | 1 |
| Glycerin | 25 | 25 |
| Distilled water | 15 | 25 |
| 10% Phosphoric acid for spraying use | 1 | 1 |
| Type of sheet | 2 | 2 |

Examples 36 to 37

Hyaluronic acid, glycerin and distilled water were placed in a plastic petri dish (diameter: 14 cm) at mixing ratios (part(s) by mass) shown in Table 9, thereby producing homogeneous and highly viscous aqueous hyaluronic acid solutions each having a thickness of about 2 cm. An area (about 2 cm×2 cm) was scooped with a spatula from each of the aqueous hyaluronic acid solutions, then immersed in a 10% phosphoric acid/glycerin solution (200 ml) for 10 minutes, then removed, and then stored at room temperature for 24 hours, thereby producing massive hyaluronic acid gels each having a size of about 2 cm×2 cm×2 cm. Subsequently, the properties of the massive hyaluronic acid gels produced in Examples 36 to 37 were evaluated in the same manner as in Examples 1 to 15. As a result, all of the massive hyaluronic acid gel were gels which were colorless and transparent, had moderate elasticity and also had a high shape retention property.

TABLE 9

| Composition of aqueous hyaluronic acid solution | Example 36 | Example 37 |
|---|---|---|
| Hyaluronic acid (1600000) | 1 | 1 |
| Glycerin | 25 | 25 |
| Distilled water | 15 | 25 |

Examples 38 to 39

Hyaluronic acid, glycerin, butanediol, 10% phosphoric acid and distilled water were mixed together at mixing ratios (part(s) by mass) shown in Table 10 using a propeller-type rotary stirrer, thereby preparing gel-forming aqueous solutions. Subsequently, each of the gel-forming aqueous solution was placed in a plastic petri dish (diameter: 9 cm) at a uniform thickness and then stored at 50° C. for 24 hours, and then a large portion of distilled water was evaporated. In this manner, hyaluronic acid gel sheets each having a thickness of about 100 μm were produced. Subsequently, the properties of the hyaluronic acid gel sheets produced in Examples 38 to 39 were evaluated in the same manner as in Examples 1 to 15. As another evaluation, pH values of aqueous hyaluronic acid solutions, each of which contained hyaluronic acid, distilled water and 10% phosphoric acid in the same amounts as those in Examples 1 to 15 but did not contain glycerin and butanediol, were measured in the same manner as in Examples 1 to 15. The results are shown in Table 10.

TABLE 10

| Composition of gel-forming aqueous solution | Example 38 | Example 39 |
|---|---|---|
| Hyaluronic acid (1600000) | 1 | 1 |
| Glycerin | 10 | 10 |
| Butanediol | 30 | 30 |
| 10% Phosphoric acid | 0.1 | 0.05 |
| Distilled water | 200 | 200 |
| PH of aqueous hyaluronic acid solution | 4.9 | 5.2 |
| Type of sheet | 1 | 2 |

From the results shown in Table 10, it is found that, when glycerin and butanediol are used in combination, even though the pH values of the aqueous hyaluronic acid solutions are as high as 4.9 or 5.2, water-soluble hyaluronic acid gels can be produced conveniently.

Examples 40 to 43

Hyaluronic acid, glycerin, butanediol, 10% phosphoric acid and distilled water were mixed together at mixing ratios (part(s) by mass) shown in Table 11 using a propeller-type rotary stirrer, thereby preparing gel-forming aqueous solutions. Subsequently, each of the gel-forming aqueous solution was placed in a plastic petri dish (diameter: 9 cm) at a uniform thickness and then stored at 50° C. for 24 hours, and then a large portion of distilled water was evaporated. In this manner, hyaluronic acid gel sheets each having a thickness of about 100 μm were produced. Subsequently, the properties of the hyaluronic acid gel sheets produced in Examples 40 to 43 were evaluated in the same manner as in Examples 1 to 15. As another evaluation, pH values of aqueous hyaluronic acid solutions, each of which contained hyaluronic acid, distilled water and 10% phosphoric acid in the same amounts as those in Examples 1 to 15 but did not contain glycerin and butanediol, were measured in the same manner as in Examples 1 to 15. The results are shown in Table 11.

TABLE 11

| Composition of gel-forming aqueous solution | | Example 40 | Example 41 | Example 42 | Example 43 |
|---|---|---|---|---|---|
| Hyaluronic acid (2300000) | | 1 | 1 | | |
| Hyaluronic acid (100000) | | | | 1 | 1 |
| Polyhydric alcohol | Glycerin | 40 | 10 | 40 | 10 |
| | Butanediol | | 30 | | 30 |
| Acid | 10% Phosphoric acid | 0.5 | 0.1 | 2 | 0.5 |
| Distilled water | | 200 | 200 | 200 | 200 |
| PH of aqueous hyaluronic acid solution | | 4.0 | 4.9 | 3.1 | 4.0 |
| Type of sheet | | 1 | 1 | 1 | 1 |

From the results shown in Table 11, it is found that, when hyaluronic acid having an average molecular weight (product labeling) of 2300000 or 100000 is used, water-soluble hyaluronic acid gels can be produced conveniently.

Examples 44 to 49

Hyaluronic acid, glycerin, butanediol, 10% phosphoric acid and distilled water were mixed together at mixing ratios (part(s) by mass) shown in Table 12 using a propeller-type rotary stirrer, thereby preparing gel-forming aqueous solutions. Subsequently, each of the gel-forming aqueous solution was placed in a plastic petri dish (diameter: 9 cm) at a uniform thickness and then stored at 50° C. for 48 hours, and then a large portion of distilled water was evaporated. In this manner, hyaluronic acid gel sheets each having a thickness of about 4 mm were produced. Subsequently, the properties of the hyaluronic acid gel sheets produced in Examples 44 to 49 were evaluated on the basis of the criteria shown below. As another evaluation, pH values of aqueous hyaluronic acid solutions, each of which contained hyaluronic acid, distilled water and 10% phosphoric acid in the same amounts as those in Examples 1 to 15 but did not contain glycerin and butanediol, were measured in the same manner as in Examples 1 to 15. The results are shown in Table 12.

<Evaluation of Properties of Hyaluronic Acid Gel Sheet>
A: A gel which was colorless and transparent, had a high shape retention property and moderate elasticity, and also had sufficient mechanical strength. The gel was not broken when the gel was lifted with hands.
B: A gel which was colorless and transparent and had a high shape retention property and moderate elasticity. A polyhydric alcohol bleed out from the gel and the mechanical strength of the gel was deteriorated compared with the gel A, but the gel was not broken when the gel was lifted with hands.
C: A gel which was colorless and transparent and had a high shape retention property and moderate elasticity. A polyhydric alcohol bleed out from the gel, the mechanical strength of the gel was deteriorated compared with the gel B, and the gel was broken when the gel was lifted with hands.

less relative to 1 part by mass of hyaluronic acid, a water-soluble hyaluronic acid gel having sufficiently high mechanical strength can be produced. It is also found that, when the content of the polyhydric alcohol is more than 500 parts by mass and 1500 parts by mass or less relative to 1 part by mass of hyaluronic acid, a soft water-soluble hyaluronic acid gel having slightly reduced mechanical strength can be produced. It is also found that, when the content of the polyhydric alcohol is more than 1500 parts by mass and 2000 parts by mass or less relative to 1 part by mass of hyaluronic acid, a water-soluble hyaluronic acid gel which has reduced mechanical strength and is soft to such an extent that the gel is broken when the gel is lifted with hands can be produced.

Examples 50 to 56

Hyaluronic acid, glycerin, butanediol, an acid (ethyl ascorbic acid, gluconolactone, lactobionic acid or aspartic acid) and distilled water were mixed together at mixing ratios (part(s) by mass) shown in Table 13 using a propeller-type rotary stirrer, thereby preparing gel-forming aqueous solutions. Subsequently, each of the gel-forming aqueous solution was placed in a plastic petri dish (diameter: 9 cm) at a uniform thickness and then stored at 50° C. for 24 hours, and then a large portion of distilled water was evaporated. In this manner, hyaluronic acid gel sheets each having a thickness of about 100 μm were produced. Subsequently, the properties of the hyaluronic acid gel sheets produced in Examples 50 to 56 were evaluated in the same manner as in Examples 1 to 15. As another evaluation, pH values of aqueous hyaluronic acid solutions, each of which contained hyaluronic acid, distilled water and the acid in the same amounts as those in Examples 1 to 15 but did not contain

TABLE 12

| Composition of gel-forming aqueous solution | Example 44 | Example 45 | Example 46 | Example 47 | Example 48 | Example 49 |
|---|---|---|---|---|---|---|
| Hyaluronic acid (2300000) | 1 | 1 | 1 | 1 | 1 | 1 |
| Glycerin | 20 | 40 | 100 | 200 | 300 | 400 |
| Butanediol | 80 | 160 | 400 | 800 | 1200 | 1600 |
| 10% Phosphoric acid | 1 | 1 | 2 | 5 | 5 | 10 |
| Distilled water | 200 | 200 | 200 | 200 | 200 | 200 |
| PH of aqueous hyaluronic acid solution | 3.7 | 3.7 | 3.1 | 2.5 | 2.5 | 2.1 |
| Type of sheet | A | A | A | B | B | C |

From the results shown in Table 12, it is found that, when the content of the polyhydric alcohol is 500 parts by mass or glycerin and butanediol, were measured in the same manner as in Examples 1 to 15. The results are shown in Table 13.

TABLE 13

| Composition of gel-forming aqueous solution | | Example 50 | Example 51 | Example 52 | Example 53 | Example 54 | Example 55 | Example 56 |
|---|---|---|---|---|---|---|---|---|
| Hyaluronic acid (1600000) | | 1 | 1 | 1 | 1 | 1 | 1 | 1 |
| Polyhydric | Glycerin | 10 | 40 | 10 | 40 | 10 | 40 | 10 |

TABLE 13-continued

| Composition of gel-forming aqueous solution | | Example 50 | Example 51 | Example 52 | Example 53 | Example 54 | Example 55 | Example 56 |
|---|---|---|---|---|---|---|---|---|
| alcohol | Butanediol | 30 | | 30 | | 30 | | 30 |
| Acid | Ethyl ascorbic acid | 20 | | | | | | |
| | Gluconolactone | | 1 | 0.5 | | | | |
| | Lactobionic acid | | | | 1 | 0.5 | | |
| | Aspartic acid | | | | | | 1 | 0.1 |
| | Distilled water | 200 | 200 | 200 | 200 | 200 | 200 | 200 |
| PH of aqueous hyaluronic acid solution | | 4.4 | 3.6 | 4.0 | 3.7 | 4.0 | 3.3 | 4.1 |
| Type of sheet | | 1 | 1 | 1 | 1 | 1 | 1 | 1 |

From the results shown in Table 13, it is found that, when ethyl ascorbic acid, gluconolactone, lactobionic acid or aspartic acid is used as the acid, a water-soluble hyaluronic acid gel can be produced conveniently.

Examples 57 to 67

Hyaluronic acid, glycerin, butanediol, PEG 200, propylene glycol, propanediol, diglycerin, pentanediol, hexanediol, 10% phosphoric acid and distilled water were mixed together at mixing ratios (part(s) by mass) shown in Table 14 using a propeller-type rotary stirrer, thereby preparing gel-forming aqueous solutions. Subsequently, each of the gel-forming aqueous solution was placed in a plastic petri dish (diameter: 9 cm) at a uniform thickness and then stored at 50° C. for 24 hours, and then a large portion of distilled water was evaporated. In this manner, hyaluronic acid gel sheets each having a thickness of about 100 μm were produced. Subsequently, the properties of the hyaluronic acid gel sheets produced in Examples 57 to 67 were evaluated in the same manner as in Examples 1 to 15. As another evaluation, pH values of aqueous hyaluronic acid solutions, each of which contained hyaluronic acid, distilled water and 10% phosphoric acid in the same amounts as those in Examples 1 to 15 but did not contain glycerin, butanediol, PEG 200, propylene glycol, propanediol, diglycerin, pentanediol and hexanediol, were measured in the same manner as in Examples 1 to 15. The results are shown in Table 14.

For reference, the gel-forming aqueous solutions used for producing the hyaluronic acid gel sheets of Examples 57, 59, 60 and 62 and the hyaluronic acid gel sheets which had been dried were weighed. The weights are as follows.

Example 57

The weight of the gel-forming aqueous solution: 4.15 g (solid content: 0.71 g)
The weight of the hyaluronic acid gel sheet: 0.72 g Example 59

The weight of the gel-forming aqueous solution: 4.10 g (solid content: 0.70 g)
The weight of the hyaluronic acid gel sheet: 0.71 g Example 60

The weight of the gel-forming aqueous solution: 4.13 g (solid content: 0.70 g)
The weight of the hyaluronic acid gel sheet: 0.65 g Example 62

The weight of the gel-forming aqueous solution: 4.10 g (solid content: 0.70 g)
The weight of the hyaluronic acid gel sheet: 0.73 g In this regard, the solid content in each of the gel-forming aqueous solutions refers to the total amount of the components used for the preparation of each of the gel-forming aqueous solutions except distilled water.

TABLE 14

| Composition of gel-forming aqueous solution | | Example 57 | Example 58 | Example 59 | Example 60 | Example 61 | Example 62 | Example 63 | Example 64 | Example 65 | Example 66 | Example 67 |
|---|---|---|---|---|---|---|---|---|---|---|---|---|
| Hyaluronic acid (1600000) | | 1 | 1 | 1 | 1 | 1 | 1 | 1 | 1 | 1 | 1 | 1 |
| Polyhydric alcohol | Glycerin | 10 | 20 | 10 | 10 | 10 | 10 | 10 | 10 | 10 | 10 | 25 |
| | Butanediol | 30 | 20 | | | | | 15 | | 15 | 30 | 15 |
| | PEG200 | | | 30 | | | | | | | | |
| | Propylene glycol | | | | 30 | | | | | | | |
| | Propanediol | | | | | 30 | | | 15 | | | |
| | Diglycerin | | | | | | 30 | | | | | |
| | Pentanediol | | | | | | | 15 | 15 | | | |
| | Hexanediol | | | | | | | | | 15 | | |
| 10% phosphoric acid | | 0.25 | 0.25 | 0.25 | 0.25 | 0.25 | 0.25 | 0.25 | 0.25 | 0.25 | 0.4 | 0.4 |
| Distilled water | | 200 | 200 | 200 | 200 | 200 | 200 | 200 | 200 | 200 | 200 | 200 |
| PH of aqueous hyaluronic acid solution | | 4.6 | 4.6 | 4.6 | 4.6 | 4.6 | 4.6 | 4.6 | 4.6 | 4.6 | 4.2 | 4.2 |
| Type of sheet | | 1 | 1 | 1 | 1 | 1 | 1 | 1 | 1 | 1 | 1 | 1 |

From the results shown in Table 14, it is found that a weakly acidic water-soluble hyaluronic acid gel can be produced conveniently when glycerin is used in combination with butanediol, PEG 200, propylene glycol, propanediol, diglycerin, pentanediol or hexanediol. It is also found that, particularly when the ratio of the amount of glycerin to the amount of another polyhydric alcohol falls within the range from 10:30 to 20:20 by mass, even though the aqueous hyaluronic acid solution has a pH value of 4.6 and is therefore significantly weakly acidic, a water-soluble hyaluronic acid gel having moderate elasticity and a high shape retention property can be produced conveniently.

Examples 68 to 75

Hyaluronic acid, glycerin, butanediol, a beauty component (collagen, hyaluronic acid (molecular weight: 10000 or less), Hyalorepair, honey), 10% phosphoric acid and distilled water were mixed together at mixing ratios (part(s) by mass) shown in Table 15 using a propeller-type rotary stirrer, thereby preparing gel-forming aqueous solutions. Subsequently, each of the gel-forming aqueous solution was placed in a plastic petri dish (diameter: 9 cm) at a uniform thickness and then stored at 50° C. for 24 hours, and then a large portion of distilled water was evaporated. In this manner, hyaluronic acid gel sheets each having a thickness of about 100 μm were produced. Subsequently, the properties of the hyaluronic acid gel sheets produced in Examples 68 to 75 were evaluated in the same manner as in Examples 1 to 15. As another evaluation, pH values of aqueous hyaluronic acid solutions, each of which contained hyaluronic acid, distilled water, the beauty component and 10% phosphoric acid in the same amounts as those in Examples 1 to 15 but did not contain glycerin and butanediol, were measured in the same manner as in Examples 1 to 15. The results are shown in Table 15.

TABLE 15

| Composition of gel-forming aqueous solution | | Example 68 | Example 69 | Example 70 | Example 71 | Example 72 | Example 73 | Example 74 | Example 75 |
|---|---|---|---|---|---|---|---|---|---|
| Hyaluronic acid (1600000) | | 1 | 1 | 1 | 1 | 1 | 1 | 1 | 1 |
| Polyhydric alcohol | Glycerin | 40 | 10 | 40 | 10 | 40 | 10 | 40 | 10 |
| | Butanediol | | 30 | | 30 | | 30 | | 30 |
| Beauty component | Collagen | 1 | 1 | | | | | | |
| | Hyaluronic acid (10000) | | | 1 | 1 | | | | |
| | Hyalorepair | | | | | 1 | 1 | | |
| | Honey | | | | | | | 1 | 1 |
| 10% Phosphoric acid | | 1 | 0.25 | 1 | 0.25 | 1 | 0.25 | 1 | 0.25 |
| Distilled water | | 200 | 200 | 200 | 200 | 200 | 200 | 200 | 200 |
| PH of aqueous hyaluronic acid solution | | 3.7 | 4.6 | 3.7 | 4.6 | 3.7 | 4.6 | 3.7 | 4.6 |
| Type of sheet | | 1 | 1 | 1 | 1 | 1 | 1 | 1 | 1 |

As shown in Table 15, it is found that a water-soluble hyaluronic acid gel having moderate elasticity and a high shape retention property can be produced conveniently even when a beauty component is added to the water-soluble hyaluronic acid gel.

Examples 76 to 78

Hyaluronic acid, glycerin, butanediol and distilled water were mixed together at mixing ratios (part(s) by mass) shown in Table 16 using a propeller-type rotary stirrer, thereby preparing aqueous hyaluronic acid solutions. Subsequently, each of the aqueous hyaluronic acid solution was placed in a plastic petri dish (diameter: 9 cm) at a uniform thickness and then stored at 50° C. for 24 hours, and then a large portion of distilled water was evaporated. In this manner, highly viscous solutions each having a thickness of about 1 mm were produced. Subsequently, 2% hydrochloric acid or acetic acid in an amount corresponding to the mixing ratio (part(s) by mass) shown in Table 16 was applied onto the surface of each of the solutions, and then the resultant products were stored at room temperature for 24 hours. In this manner, hyaluronic acid gel sheets were produced. Subsequently, the properties of the hyaluronic acid gel sheets produced in Examples 76 to 78 were evaluated in the same manner as in Examples 1 to 15. The results are shown in Table 16.

TABLE 16

| | Example 76 | Example 77 | Example 78 |
|---|---|---|---|
| Hyaluronic acid (1600000) | 1 | 1 | 1 |
| Glycerin | 40 | 40 | 40 |
| 2% Hydrochloric acid | 5 | | |
| Acetic acid | | 5 | 1 |
| Distilled water | 200 | 200 | 200 |
| Type of sheet | 1 | 1 | 1 |

Hydrochloric acid, acetic acid and the like is evaporated easily together with water when a drying procedure is carried out during the production of a water-soluble hyaluronic acid gel, and therefore it may be difficult to control the content of the acid in accordance with a production method employed. Consequently, a water-soluble hyaluronic acid gel having moderate elasticity cannot be produced easily (see, for example, Example 14). However, it is found that, as in the case of Examples 76 to 78, a water-soluble hyaluronic acid gel having moderate elasticity and a high shape retention property can be produced by evaporating water from an aqueous hyaluronic acid solution and then applying the acid.

Examples 79 to 82

Hyaluronic acid having a high molecular weight (average molecular weight: 2300000), glycerin, butanediol, 10% phosphoric acid and distilled water were mixed together at mixing ratios (part(s) by mass) shown in Table 17 using a propeller-type rotary stirrer, thereby preparing gel-forming aqueous solutions. Subsequently, each of the gel-forming aqueous solution was placed in a plastic petri dish (diameter: 9 cm) at a uniform thickness and then stored at 50° C. for 24 hours, and then a large portion of distilled water was evaporated. In this manner, hyaluronic acid gel sheets each having a thickness of about 100 μm were produced. Subsequently, the properties of the hyaluronic acid gel sheets produced in Examples 79 to 82 were evaluated in the same manner as in Examples 1 to 15. As another evaluation, pH values of aqueous hyaluronic acid solutions, each of which contained hyaluronic acid, distilled water and 10% phosphoric acid in the same amounts as those in Examples 1 to 15 but did not contain glycerin and butanediol, were measured in the same manner as in Examples 1 to 15. The results are shown in Table 17.

TABLE 17

| Composition of gel-forming aqueous solution | Example 79 | Example 80 | Example 81 | Example 82 |
|---|---|---|---|---|
| Hyaluronic acid (2300000) | 1 | 1 | 1 | 1 |
| Glycerin | 7.5 | 10 | 10 | 20 |
| Butanediol | 2.5 | 30 | 90 | 80 |
| 10% Phosphoric acid | 0.05 | 0.05 | 0.25 | 0.25 |
| Distilled water | 200 | 200 | 200 | 200 |
| PH of aqueous hyaluronic acid solution | 5.2 | 5.2 | 4.6 | 4.6 |
| Type of sheet | 1 | 1 | 1 | 1 |

As shown in Table 17, it is found that a water-soluble hyaluronic acid gel having moderate elasticity and a high shape retention property can be produced conveniently by using hyaluronic acid having a high molecular weight and using glycerin and butanediol in combination even if the acidity of the aqueous hyaluronic acid solution is weakened to a pH value of 4.6 or 5.2. For example, in Example 39 mentioned above, the rating of the property evaluation on the water-soluble hyaluronic acid gel was "2" when sodium hyaluronate having an average molecular weight of 1600000 was used. In Example 80, however, the rating of the property evaluation on the water-soluble hyaluronic acid gel was "1" when sodium hyaluronate having a high molecular weight, i.e., an average molecular weight of 2300000, was used.

Examples 83 to 86

Hyaluronic acid (average molecular weight: 1600000) was dissolved in distilled water and then glycerin and butanediol were added thereto at mixing ratios (part(s) by mass) shown in Table 18, and then each of the resultant mixtures was agitated using a propeller-type rotary stirrer, thereby preparing aqueous hyaluronic acid solutions. Subsequently, each of the aqueous hyaluronic acid solution was placed in a plastic petri dish (diameter: 9 cm) at a uniform thickness and then stored at 50° C. for 24 hours, and then a large portion of distilled water was evaporated. In this manner, highly viscous solutions each having a thickness of about 1 mm were produced. Subsequently, 10% phosphoric acid and distilled water were applied in amounts corresponding to the mixing ratios (part(s) by mass) shown in Table 18 onto each of the highly viscous solutions, and then the resultant products were stored at room temperature for 48 hours, thereby producing hyaluronic acid gel sheets. Subsequently, the properties of the hyaluronic acid gel sheets produced in Examples 83 to 86 were evaluated in the same manner as in Examples 1 to 15. The results are shown in Table 18.

TABLE 18

|  | Example 83 | Example 84 | Example 85 | Example 86 |
|---|---|---|---|---|
| Hyaluronic acid (1600000) | 1 | 1 | 1 | 1 |
| Glycerin | 10 | 10 | 10 | 10 |
| Butanediol | 30 | 30 | 30 | 30 |
| Distilled water | 200 | 200 | 200 | 200 |
| 10% Phosphoric acid | 1 | 1 | 1 | 1 |
| Distilled water for application use | 40 | 60 | 80 | 100 |
| Type of sheet | 1 | 1 | 2 | 3 |

As shown in Table 18, it is found that, in the present invention, a gel can be formed even when water is contained in an amount of about 100 parts by mass relative to 1 part by mass of hyaluronic acid. It is also found that the rating of the properties of the gel is "1" when the content of water is about 60 parts by mass or less and a gel that is colorless and transparent, has moderate elasticity and also has a high shape retention property can be produced.

Examples 87 to 96

Hyaluronic acid (average molecular weight: 1600000 or 2300000) was dissolved in distilled water and then glycerin and butanediol were added thereto at mixing ratios (part(s) by mass) shown in Table 19, and then each of the resultant mixtures was agitated using a propeller-type rotary stirrer, thereby preparing aqueous hyaluronic acid solutions. Subsequently, each of the aqueous hyaluronic acid solution was placed in a plastic petri dish (diameter: 9 cm) at a uniform thickness and then stored at 50° C. for 24 hours, and then a large portion of distilled water was evaporated. In this manner, highly viscous solutions each having a thickness of about 200 μm were produced. Subsequently, 10% phosphoric acid and distilled water were applied in amounts corresponding to the mixing ratios (part(s) by mass) shown in Table 19 onto each of the highly viscous solutions, and the resultant products were stored at room temperature for 48 hours, thereby producing hyaluronic acid gel sheets. Subsequently, the properties of the hyaluronic acid gel sheets produced were evaluated on the basis of the criteria shown below. The results are shown in Table 19.

<Evaluation of Properties of Hyaluronic Acid Gel Sheet>

A': A gel which was colorless and transparent, had a high shape retention property and moderate elasticity, and also had sufficient mechanical strength. The gel was not broken when the gel was lifted with hands.

B': A gel which was colorless and transparent and had a high shape retention property and moderate elasticity. The mechanical strength of the gel was deteriorated compared with the gel A, but the gel was not broken when the gel was lifted with hands.

C': A gel which was colorless and transparent and had a high shape retention property and moderate elasticity. The mechanical strength of the gel was deteriorated compared with the gel B, and the gel was broken when the gel was lifted with hands.

TABLE 19

|  | Example 87 | Example 88 | Example 89 | Example 90 | Example 91 | Example 92 | Example 93 | Example 94 | Example 95 | Example 96 |
|---|---|---|---|---|---|---|---|---|---|---|
| Hyaluronic acid (1600000) | 1 | 1 | 1 | 1 | 1 | 1 | | | | |
| Hyaluronic acid (2300000) | | | | | | | 1 | 1 | 1 | 1 |
| Glycerin | 10 | 10 | 10 | 10 | 10 | 10 | 10 | 10 | 10 | 10 |
| Butanediol | 30 | 30 | 30 | 30 | 30 | 30 | 30 | 30 | 30 | 30 |
| Distilled water | 200 | 200 | 200 | 200 | 200 | 200 | 200 | 200 | 200 | 200 |
| 10% Phosphoric acid | 2 | 2 | 3 | 3 | 4 | 4 | 4 | 5 | 6 | 6 |
| Distilled water for application use | 80 | 100 | 150 | 200 | 300 | 400 | 400 | 500 | 600 | 700 |
| Type of sheet | A' | A' | A' | A' | B' | C' | A' | B' | B' | C' |

As shown in Table 19, it is found that, in the present invention, a gel having high mechanical strength can be produced using hyaluronic acid having a high molecular weight or increasing the content of the acid even when water is contained in the gel in an amount of about 400 parts by mass relative to 1 part by mass of hyaluronic acid for example.

Examples 97 and 98

Hyaluronic acid (average molecular weight: 1600000 or 2300000) was dissolved in distilled water and then 10% phosphoric acid, glycerin and butanediol were added thereto at mixing ratios (part(s) by mass) shown in Table 20, and then each of the resultant mixtures was agitated using a propeller-type rotary stirrer, thereby preparing gel-forming aqueous solutions. Subsequently, each of the aqueous solution was placed in a plastic petri dish (diameter: 9 cm) at a uniform thickness and then stored at 50° C. for 24 hours, and then a large portion of distilled water was evaporated. In this manner, water-soluble hyaluronic acid gels each having a thickness of about 200 µm were produced. Subsequently, distilled water was applied in an amount corresponding to the mixing ratio (parts by mass) shown in Table 20 onto each of the water-soluble hyaluronic acid gels, and then the resultant products were stored at room temperature for 48 hours, thereby producing hyaluronic acid gel sheets. Subsequently, the properties of the hyaluronic acid gel sheets produced were evaluated in the same manner as in Examples 87 to 96. The results are shown in Table 20.

TABLE 20

|  | Example 97 | Example 98 |
|---|---|---|
| Hyaluronic acid (1600000) | 1 | |
| Hyaluronic acid (2300000) | | 1 |
| Glycerin | 10 | 10 |
| Butanediol | 30 | 30 |
| 10% Phosphoric acid | 3 | 4 |
| Distilled water | 1000 | 1000 |
| Distilled water for application use | 200 | 400 |
| Type of sheet | A' | A' |

As shown in Table 20, it is found that, in the present invention, as in the case of Examples 87 to 96, a gel having high mechanical strength can be produced by adding water to a hyaluronic acid gel even when water is contained in an amount of about 200 to about 400 parts by mass relative to 1 part by mass of hyaluronic acid for example.

Examples 99 to 102

Hyaluronic acid, glycerin, butanediol, 10% phosphoric acid and distilled water were mixed together at mixing ratios (part(s) by mass) shown in Table 14 using a propeller-type rotary stirrer in the same manner as in Example 57, thereby preparing gel-forming aqueous solutions. Subsequently, each of the gel-forming aqueous solution was applied at a uniform thickness onto the non-woven fabric side of a laminate film composed of a polyethylene terephthalate film (thickness 7.5 µm) and a polyethylene terephthalate non-woven fabric (a product name: "EH-1212", Japan Vilene Company, Ltd.), then each of the resultant products was stored at 50° C. for 24 hours, and then a large portion of distilled water was evaporated. In this manner, hyaluronic acid gel sheets each integrated with the laminate film (four types of hyaluronic acid gel sheets, in which the thicknesses of the hyaluronic acid gel sheets were about 10 µm, about 20 µm, about 50 µm and 200 µm) were produced. In all of the products, the adhesion strength between the laminate film and the hyaluronic acid gel sheet was sufficient.

The invention claimed is:

1. A water-soluble hyaluronic acid gel comprising hyaluronic acid acting as a gelling agent, a polyhydric alcohol, an acid and 0 to 10% by mass of a water-soluble organic solvent,
    wherein the polyhydric alcohol comprises glycerin and a polyhydric alcohol other than glycerin at a ratio of 30:10 to 4:36 by mass,
    wherein a content of hyaluronic acid is 0.2% by mass or more, and
    wherein the water-soluble hyaluronic acid gel has high mechanical strength and a shape retention property, the high mechanical strength refers to strength to such an extent that a sheet made from the water-soluble hyaluronic acid gel which has a thickness of about 100 µm cannot be broken even when the sheet is held between fingers and is then pulled up.

2. The water-soluble hyaluronic acid gel according to claim 1, wherein the water-soluble hyaluronic acid gel is produced from an aqueous hyaluronic acid solution having a pH value falling within the range from 1.9 to 5.2, in which the aqueous hyaluronic acid solution is prepared by dissolving the components to be contained in the water-soluble hyaluronic acid gel, except the polyhydric alcohol and water, in water in such a manner that 200 parts by mass of water is contained relative to 1 part by mass of hyaluronic acid contained in the water-soluble hyaluronic acid gel.

3. The water-soluble hyaluronic acid gel according to claim 1, wherein the content of hyaluronic acid is 0.2 to 20% by mass.

4. The water-soluble hyaluronic acid gel according to claim 1, wherein the polyhydric alcohol is contained in an amount of 1 to 2000 parts by mass inclusive relative to 1 part by mass of hyaluronic acid.

5. The water-soluble hyaluronic acid gel according to claim 1, wherein water is contained in an amount of 700 parts by mass or less relative to 1 part by mass of hyaluronic acid.

6. The water-soluble hyaluronic acid gel according to claim 1, wherein the polyhydric alcohol comprises glycerin and a polyhydric alcohol other than glycerin at a ratio of 25:15 to 4:36 by mass.

7. The water-soluble hyaluronic acid gel according to claim 6, wherein the water-soluble hyaluronic acid gel is produced from an aqueous hyaluronic acid solution having a pH value falling within the range from 4.2 to 5.2, in which the aqueous hyaluronic acid solution is prepared by dissolving the components to be contained in the water-soluble hyaluronic acid gel, except the polyhydric alcohol and water, in water in such a manner that 200 parts by mass of water is contained relative to 1 part by mass of hyaluronic acid contained in the water-soluble hyaluronic acid gel.

8. The water-soluble hyaluronic acid gel according to claim 1, having a sheet form.

9. A water-soluble hyaluronic acid gel sheet comprising: a support material; and a water-soluble hyaluronic acid gel as recited in claim 1 which is formed on the support material.

10. A cosmetic comprising a water-soluble hyaluronic acid gel as recited in claim 1.

11. A pharmaceutical composition for external applications, comprising a water-soluble hyaluronic acid gel as recited in claim 1.

12. A composition for medical tools, comprising a water-soluble hyaluronic acid gel as recited in claim 1.

13. A method for producing a water-soluble hyaluronic acid gel, comprising a step of mixing hyaluronic acid, a polyhydric alcohol, an acid, 0 to 10% by mass of a water-soluble organic solvent and water together to prepare a gel-forming aqueous solution,
  wherein the water-soluble hyaluronic acid gel comprises the hyaluronic acid acting as a gelling agent, the polyhydric alcohol, the acid and 0 to 10% by mass of the water-soluble organic solvent,
  wherein the polyhydric alcohol comprises glycerin and a polyhydric alcohol other than glycerin at a ratio of 30:10 to 4:36 by mass,
  wherein a content of hyaluronic acid is 0.2% by mass or more, and
  wherein the water-soluble hyaluronic acid gel has high mechanical strength and a shape retention property, the high mechanical strength refers to strength to such an extent that a sheet made from the water-soluble hyaluronic acid gel which has a thickness of about 100 μm cannot be broken even when the sheet is held between fingers and is then pulled up.

14. The method for producing a water-soluble hyaluronic acid gel according to claim 13, further comprising a step of evaporating water contained in the gel-forming aqueous solution.

15. The method for producing a water-soluble hyaluronic acid gel according to claim 14, wherein the evaporation of water is carried out in such a state that the gel-forming aqueous solution is placed in a container.

16. The method for producing a water-soluble hyaluronic acid gel according to claim 14, further comprising a step of adding water after water contained in the gel-forming aqueous solution is evaporated.

17. A method for producing a water-soluble hyaluronic acid gel, comprising: a step of mixing hyaluronic acid, a polyhydric alcohol, 0 to 10% by mass of a water-soluble organic solvent and water together to prepare an aqueous hyaluronic acid solution; and a step of adding an acid to the aqueous hyaluronic acid solution,
  wherein the water-soluble hyaluronic acid gel comprises the hyaluronic acid acting as a gelling agent, the polyhydric alcohol, the acid and 0 to 10% by mass of the water-soluble organic solvent,
  wherein the polyhydric alcohol comprises glycerin and a polyhydric alcohol other than glycerin at a ratio of 30:10 to 4:36 by mass,
  wherein a content of hyaluronic acid is 0.2% by mass or more, and
  wherein the water-soluble hyaluronic acid gel has high mechanical strength and a shape retention property, the high mechanical strength refers to strength to such an extent that a sheet made from the water-soluble hyaluronic acid gel which has a thickness of about 100 μm cannot be broken even when the sheet is held between fingers and is then pulled up.

18. A method for producing a water-soluble hyaluronic acid gel, comprising: a step of mixing hyaluronic acid, a polyhydric alcohol, 0 to 10% by mass of a water-soluble organic solvent and water together to prepare an aqueous hyaluronic acid solution; a step of drying the aqueous hyaluronic acid solution; and a step of adding an acid to the dried aqueous hyaluronic acid solution,
  wherein the water-soluble hyaluronic acid gel comprises the hyaluronic acid acting as a gelling agent, the polyhydric alcohol, the acid and 0 to 10% by mass of the water-soluble organic solvent,
  wherein the polyhydric alcohol comprises glycerin and a polyhydric alcohol other than glycerin at a ratio of 30:10 to 4:36 by mass,
  wherein a content of hyaluronic acid is 0.2% by mass or more, and
  wherein the water-soluble hyaluronic acid gel has high mechanical strength and a shape retention property, the high mechanical strength refers to such an extent that a sheet made from the water-soluble hyaluronic acid gel which has a thickness of about 100 μm cannot be broken even when the sheet is held between fingers and is then pulled up.

* * * * *